United States Patent
Gebhardt et al.

(10) Patent No.: US 7,435,874 B2
(45) Date of Patent: Oct. 14, 2008

(54) PLANT RESISTANCE GENE

(76) Inventors: Christiane Gebhardt, Vollrathstrasse 21, 50226 Frechen (DE); Agim Ballvora, Teutonenstrasse 30, 53175 Bonn (DE); Maria Raffaella Ercolano, Corso Italia 238/B, 80063 Piano di Sorrento (IT); Julia Weiss, Isla de Pascua 41, El Limonar, 30868 Isla Plana, Cartagena (ES); Francesco Salamini, Carl von Linne Weg 1, 50829 Koln (DE)

(*) Notice: Subject to any disclaimer, the term of this patent is extended or adjusted under 35 U.S.C. 154(b) by 116 days.

(21) Appl. No.: 10/488,228

(22) PCT Filed: Aug. 30, 2002

(86) PCT No.: PCT/EP02/09738

§ 371 (c)(1),
(2), (4) Date: Aug. 17, 2004

(87) PCT Pub. No.: WO03/020013

PCT Pub. Date: Mar. 13, 2003

(65) Prior Publication Data

US 2005/0076406 A1   Apr. 7, 2005

(30) Foreign Application Priority Data

Aug. 31, 2001   (EP)  .................................. 01120670

(51) Int. Cl.
*A01H 5/00*   (2006.01)
*C12N 15/29*  (2006.01)
*C12N 15/82*  (2006.01)

(52) U.S. Cl. .................. 800/279; 800/278; 800/298; 800/295; 435/320.1; 435/69.1; 435/468; 536/23.6

(58) Field of Classification Search ................ 536/23.6; 435/320.1, 468, 278, 279, 298; 800/279
See application file for complete search history.

(56) References Cited

U.S. PATENT DOCUMENTS 5,859,351 A * 1/1999 Staskawicz et al. ......... 800/301

OTHER PUBLICATIONS

Parker et al (The Plant Cell (1996), vol. 8, pp. 2033-2046).*
Leister et al., "A PCR-based approach for isolating pathogen resistance genes from potato with potential for wide application in plants," Nature Genetics Dec. 1996; vol. 14; pp. 421-429.

* cited by examiner

*Primary Examiner*—Medina A Ibrahim
(74) *Attorney, Agent, or Firm*—Akerman Senterfitt

(57) ABSTRACT

Disclosed are isolated nucleic acid molecules from *Solanum tuberosum* which are capable of conferring resistance against plant pathogens including *Phytophthora infestans*. Transgenic plants and plant cells comprising the nucleic acid molecules are also disclosed.

7 Claims, 5 Drawing Sheets

SEQUENCE LISTING

<160> NUMBER OF SEQ ID NOS: 12

<210> SEQ ID NO 1
<211> LENGTH: 10388
<212> TYPE: DNA
<213> ORGANISM: Solanum tuberosum
<220> FEATURE:
<221> NAME/KEY: Intron
<222> LOCATION: (4878)..(4970)
<223> OTHER INFORMATION:
<220> FEATURE:
<221> NAME/KEY: Intron
<222> LOCATION: (6103)..(6229)
<223> OTHER INFORMATION:
<220> FEATURE:
<221> NAME/KEY: Intron
<222> LOCATION: (6323)..(6404)
<223> OTHER INFORMATION:
<220> FEATURE:
<221> NAME/KEY: CDS
<222> LOCATION: (2223)..(4877)
<223> OTHER INFORMATION:
<220> FEATURE:
<221> NAME/KEY: CDS
<222> LOCATION: (4971)..(6102)
<223> OTHER INFORMATION:
<220> FEATURE:
<221> NAME/KEY: CDS
<222> LOCATION: (6230)..(6321)
<223> OTHER INFORMATION:
<220> FEATURE:
<221> NAME/KEY: 5'UTR
<222> LOCATION: (2164)..(2222)
<223> OTHER INFORMATION:
<220> FEATURE:
<221> NAME/KEY: promoter
<222> LOCATION: (1)..(2164)
<223> OTHER INFORMATION:
<220> FEATURE:
<221> NAME/KEY: 3'UTR
<222> LOCATION: (6405)..(6702)
<223> OTHER INFORMATION:

<400> SEQUENCE: 1
ttaatatata gatggaatcg gtgttttaaa aggcagggcg cgaggcgaga cgttttactt        60
agtatagagc gaggcgtaag cctaatgatt cattttctcta agaacgatat taattcatta      120
aattacttaa ttataataaa tttatacact tcaaatacac ttggatatga ataagtaatt      180
atccttcacg agattcaaat gaaaataag tggagttaat tagagtaaag tagagtaatt       240
taaacacttt agtctgaatc tttatacatt atacaaaaaa agtaattata tttcaccaaa      300
ttcaaatgga aattaaaaat atatgaagat aattacaaca caagtgttat gtgtcagttg      360
gaaagctcaa gcgtgggtcc taccatactc catgacattt cacttttagg gtatgattcg      420
taatttaatg aaaatgatga ccttttttt tggagttagt aatgaggtct aaataactaa       480
acatagagga caaccctctt aagcaagcaa atcttgcaat aacatttcaa agaccatgat      540
atcctcaaat tttttattaa tgactaaaaa ctaacatgtt aaactctcct gtgtattatt      600
cattgtaata ttttttttgg ttaaatcatt cattgtaaaa taaattcatt atacataatg      660 ttaattttt cttaataatc aaatattatt catcgtatat ttactaaaaa tattcaatgt       720
atgatgatga gagaataaac tatataagaa atataagaaa tttaatgaaa ccatattcaa      780
aaatggcttc tcaatgtgtc aaaaaatcaa caatgacaga tcaaatacat tatcttattt      840
ctttaaattg tgttagatat atttgtactt ttagaggatt attaatttat aatatcaatg      900
aagccatata tttatataag agtcttctga aaatatatta tcttattatc ttatcaaaat      960

```
ggatgatttt ttccattgat ccaagtcggg accaaaaaag aatattatct caaagagatt      1020
attaatttac caaatattaa tttagtgagg ttttactgta atttgggtgt ggtccatgac      1080
catatatatt ttgaaaaaaa actgctttgt aaattccaag ttggaacgac atttctacag      1140
ccaatgttga aatactattc ttgtcctgat taggagactt attatttcat ttcatatata      1200
gataggtccc ttgagaacta gaaagattaa attaaagatt gagatccaat aatgcatatg      1260
aacacagaac atttgtcttt tttccaaagg ggaccatata tatataagat gtcattgtgc      1320
tttatgtatg gaagagagaa taacgatctc atatatatat ctcatatata tatatatcat      1380
ctaaaataag atgttttaaa ccatctggta ttcggtatac aatttacact aaaaagacca      1440
aacaggtggg aaggacacaa acattagatc aaaaattaag gttaagtgat tcagatatca      1500
agaggaacaa tatactaatt ggaacaaatt aaagtatcct cacttacaat ggtcatatat      1560
agaagctact taggtaatac tctcactatc cctaattatt tgtccacttt taaattagca      1620
cacctattaa taaaacaatt attggcatag tgagtttacc attttacctt tttaattatg      1680
aagcgaatga attaaaaact taagatatta aaaaaattct gcctttaaca aagtaattat      1740
ttgagggtat aataggtaaa aagaaattgt cctttttttta tttgtcaaaa tgaacaagta      1800
gttagggaca actaaaaaag gaaaaatgga tgagtaatta ggaacggagg gagtataaaa      1860
cactgtcatc actcaaaaaa tatgagtatc ttgacttgca caacataggt acttaatcaa      1920
agactcaata tacaaatctc taaagtaaat ttgtatttgt atatacagtc tctttgaaag      1980
cccaatttgt ataaaatatt taaatgcagc tagatataca aacggaaatt agcatagcaa      2040
ctgaaactat agatatagaa cataattagg caatgacttt gttttttgtt tgtctgcctc      2100
acactttatt tgactgcctt ccttgaatac tttgaatatt ctaagtacgc cagctataag      2160
gtgaagaaag aattaaacta taatactctg tattgctctt cttccataat agtgtaacaa      2220
gg atg aat ttc aac aat gaa ttg tct gat ctg aaa aat cgc ttc cta           2267
   Met Asn Phe Asn Asn Glu Leu Ser Asp Leu Lys Asn Arg Phe Leu
   1               5                   10                  15
ttt agg acg ctg aga gcc cag aaa tgc tcg gat gtt gca aga gat cga        2315
Phe Arg Thr Leu Arg Ala Gln Lys Cys Ser Asp Val Ala Arg Asp Arg
                20                  25                  30
ata gat ttc ttt ata tgg gag tta aaa ttc ctt aat tgt ttt ctc cat        2363
Ile Asp Phe Phe Ile Trp Glu Leu Lys Phe Leu Asn Cys Phe Leu His
            35                  40                  45
ttg cag agc ttc gct ttt gca agt gaa tgt ggt atg cta gat atc tca        2411
Leu Gln Ser Phe Ala Phe Ala Ser Glu Cys Gly Met Leu Asp Ile Ser
        50                  55                  60
cag aaa atg ata gaa att tgc aag agg ttt aat aca cca cct cca cat        2459
Gln Lys Met Ile Glu Ile Cys Lys Arg Phe Asn Thr Pro Pro Pro His
    65                  70                  75
aat tca ttt gca tac tgg aag gag gta att tgc aag agg ctg tgc gct        2507
Asn Ser Phe Ala Tyr Trp Lys Glu Val Ile Cys Lys Arg Leu Cys Ala
80                  85                  90                  95
att agc atc cag ccg gat gct agt tca gat gat gga ttt gca tgc tgg        2555
Ile Ser Ile Gln Pro Asp Ala Ser Ser Asp Asp Gly Phe Ala Cys Trp
                100                 105                 110
aag aaa gta att tgg aag act aag caa gaa ttc aga gct aaa tac tcc        2603
Lys Lys Val Ile Trp Lys Thr Lys Gln Glu Phe Arg Ala Lys Tyr Ser
            115                 120                 125
ttt cca aaa aca cta ctt gca gac aac aag gta tat gat gat gat gat        2651
Phe Pro Lys Thr Leu Leu Ala Asp Asn Lys Val Tyr Asp Asp Asp Asp
        130                 135                 140
```

```
                                            -continued
act aat ccc aaa ttt gtg atg gaa ttc atc gat gct gtt gtg ggg aat    2699
Thr Asn Pro Lys Phe Val Met Glu Phe Ile Asp Ala Val Val Gly Asn
145                 150                 155 ctc aat gtt cta gtc aag atc aat gat cca tct tca ttg ctt ttt gtt    2747
Leu Asn Val Leu Val Lys Ile Asn Asp Pro Ser Ser Leu Leu Phe Val
160                 165                 170                 175 cca gga ccc aag gaa caa ata gaa caa gtg tta aag gag ttg aag tta    2795
Pro Gly Pro Lys Glu Gln Ile Glu Gln Val Leu Lys Glu Leu Lys Leu
                180                 185                 190 ttg aga ttt ttt gtc tgc ttt gtt tca aac aaa tgt ata gag cct caa    2843
Leu Arg Phe Phe Val Cys Phe Val Ser Asn Lys Cys Ile Glu Pro Gln
            195                 200                 205 tac caa cat act act ttt tat act cac gct tta att gag gct agc cac    2891
Tyr Gln His Thr Thr Phe Tyr Thr His Ala Leu Ile Glu Ala Ser His
        210                 215                 220 atc gca atg gtt gtg tgg ttg aat ttg cca atc tat gga aac aga aat    2939
Ile Ala Met Val Val Trp Leu Asn Leu Pro Ile Tyr Gly Asn Arg Asn
225                 230                 235 caa gac ttg gct tca agt gaa gtt agt tgt ttg ctt tct gat ttc atg    2987
Gln Asp Leu Ala Ser Ser Glu Val Ser Cys Leu Leu Ser Asp Phe Met
240                 245                 250                 255 gaa atg aag att aag tcc att cag cca gac atc agc cgc aac aat att    3035
Glu Met Lys Ile Lys Ser Ile Gln Pro Asp Ile Ser Arg Asn Asn Ile
                260                 265                 270 tat att gat gtc ttg agg gcg ttg aag tca acc ata cca caa gct caa    3083
Tyr Ile Asp Val Leu Arg Ala Leu Lys Ser Thr Ile Pro Gln Ala Gln
            275                 280                 285 gat aag cat gct gct gag agt ggc att gtg gag act cca aca cac aat    3131
Asp Lys His Ala Ala Glu Ser Gly Ile Val Glu Thr Pro Thr His Asn
        290                 295                 300 ctg atg gtt ggt ttg agt gat caa atg gcc aac ctt cag gag atg ctc    3179
Leu Met Val Gly Leu Ser Asp Gln Met Ala Asn Leu Gln Glu Met Leu
305                 310                 315 tgc ctt cta aga gac aat ctc att cat ctg cca ata cta gat ctg gaa    3227
Cys Leu Leu Arg Asp Asn Leu Ile His Leu Pro Ile Leu Asp Leu Glu
320                 325                 330                 335 ttt cat ctt caa gat atg gat tct gtt att gtt gat gcc gga ctt ctt    3275
Phe His Leu Gln Asp Met Asp Ser Val Ile Val Asp Ala Gly Leu Leu
                340                 345                 350 att tac tca tta tat gat atc aag ggg cag aag gaa gac aca aca ttg    3323
Ile Tyr Ser Leu Tyr Asp Ile Lys Gly Gln Lys Glu Asp Thr Thr Leu
            355                 360                 365 gag gat atc aac cag gca ctt ggt ttt gat ctt ccc aga aac att gag    3371
Glu Asp Ile Asn Gln Ala Leu Gly Phe Asp Leu Pro Arg Asn Ile Glu
        370                 375                 380 cct atc aag gca atg atc aac ctt gtc atg caa aag gca ttt caa tgt    3419
Pro Ile Lys Ala Met Ile Asn Leu Val Met Gln Lys Ala Phe Gln Cys
385                 390                 395 aac ttg cca agg att cat gga cta ggt tat gtc gat ttt cta ttg aaa    3467
Asn Leu Pro Arg Ile His Gly Leu Gly Tyr Val Asp Phe Leu Leu Lys
400                 405                 410                 415 aac ctg aag gat ttc caa ggc cgt tat tca gat tca ctc gat ttc ctc    3515
Asn Leu Lys Asp Phe Gln Gly Arg Tyr Ser Asp Ser Leu Asp Phe Leu
                420                 425                 430 aag aat caa ctt caa gtt att caa act gaa ttt gag agc ttg caa cct    3563
Lys Asn Gln Leu Gln Val Ile Gln Thr Glu Phe Glu Ser Leu Gln Pro
            435                 440                 445 ttc ttg aag gtt gtc gta gaa gag cca cac aat aag ctc aag aca ctg    3611
Phe Leu Lys Val Val Val Glu Glu Pro His Asn Lys Leu Lys Thr Leu
        450                 455                 460
```

```
aat gaa gat tgt gct aca cag ata att agg aaa gca tat gag gtg gaa    3659
Asn Glu Asp Cys Ala Thr Gln Ile Ile Arg Lys Ala Tyr Glu Val Glu
    465                 470                 475 tat gta gtt gat gct tgt ata aac aaa gag gtt cct cag tgg tgc atc    3707
Tyr Val Asp Ala Cys Ile Asn Lys Glu Val Pro Gln Trp Cys Ile
480                 485                 490                 495 gag cgt tgg ctc ctg gat atc ata gag gag att act tgt atc aaa gca    3755
Glu Arg Trp Leu Leu Asp Ile Ile Glu Glu Ile Thr Cys Ile Lys Ala
                500                 505                 510 aag att cag gaa aag aac acg gtt gag gat aca atg aag act gtc att    3803
Lys Ile Gln Glu Lys Asn Thr Val Glu Asp Thr Met Lys Thr Val Ile
            515                 520                 525 gct cgt aca tca tca aaa ctg gca agg act cca agg atg aat gaa gag    3851
Ala Arg Thr Ser Ser Lys Leu Ala Arg Thr Pro Arg Met Asn Glu Glu
        530                 535                 540 att gtt ggg ttt gag gat gtc ata gaa aat tta aga aaa aaa cta ctg    3899
Ile Val Gly Phe Glu Asp Val Ile Glu Asn Leu Arg Lys Lys Leu Leu
    545                 550                 555 aat gga acc aaa ggg caa gat gtc att tca att cac ggc atg cca ggt    3947
Asn Gly Thr Lys Gly Gln Asp Val Ile Ser Ile His Gly Met Pro Gly
560                 565                 570                 575 tta ggt aag acg act tta gcc aac agt ctc tat tct gac agg tca gtt    3995
Leu Gly Lys Thr Thr Leu Ala Asn Ser Leu Tyr Ser Asp Arg Ser Val
                580                 585                 590 ttt tct caa ttt gat att tgt gca caa tgt tgt gtg tct caa gta tat    4043
Phe Ser Gln Phe Asp Ile Cys Ala Gln Cys Cys Val Ser Gln Val Tyr
            595                 600                 605 tct tat aag gac tta ata ttg gcc ttg cta cgt gat gct att ggt gag    4091
Ser Tyr Lys Asp Leu Ile Leu Ala Leu Leu Arg Asp Ala Ile Gly Glu
        610                 615                 620 ggt tct gtg cgt aga gaa ctt cat gcc aat gaa tta gct gat atg ctt    4139
Gly Ser Val Arg Arg Glu Leu His Ala Asn Glu Leu Ala Asp Met Leu
    625                 630                 635 cgc aaa act cta ttg ccc cga agg tac ctt atc ctt gtt gat gac gtg    4187
Arg Lys Thr Leu Leu Pro Arg Arg Tyr Leu Ile Leu Val Asp Asp Val
640                 645                 650                 655 tgg gaa aat agt gtt tgg gat gat tta aga ggt tgt ttt cca gat gtc    4235
Trp Glu Asn Ser Val Trp Asp Asp Leu Arg Gly Cys Phe Pro Asp Val
                660                 665                 670 aat aac aga agc aga atc att cta aca aca aga cat cat gaa gtt gcc    4283
Asn Asn Arg Ser Arg Ile Ile Leu Thr Thr Arg His His Glu Val Ala
            675                 680                 685 aaa tat gct agt gtt cat agt gat ccc ctt cat ctt cgt atg ttt gac    4331
Lys Tyr Ala Ser Val His Ser Asp Pro Leu His Leu Arg Met Phe Asp
        690                 695                 700 gaa gtt gaa agt tgg aag ttg ctt gaa aag aaa gtg ttt ggt gaa gaa    4379
Glu Val Glu Ser Trp Lys Leu Leu Glu Lys Lys Val Phe Gly Glu Glu
    705                 710                 715 agc tgt tcc cct ctc cta aaa aat gtt ggg cta aga ata gca aaa atg    4427
Ser Cys Ser Pro Leu Leu Lys Asn Val Gly Leu Arg Ile Ala Lys Met
720                 725                 730                 735 tgt gga caa cta cct ctt tca att gtt ctg gtg gct ggt att ctg tca    4475
Cys Gly Gln Leu Pro Leu Ser Ile Val Leu Val Ala Gly Ile Leu Ser
                740                 745                 750 gag atg gaa aag gaa gta gaa tgt tgg gaa caa gtg gcc aac aat ttg    4523
Glu Met Glu Lys Glu Val Glu Cys Trp Glu Gln Val Ala Asn Asn Leu
            755                 760                 765 ggt tcc tac att cac aat gac tca aga gcc att gta gac aaa agt tat    4571
Gly Ser Tyr Ile His Asn Asp Ser Arg Ala Ile Val Asp Lys Ser Tyr
```

-continued

```
            770             775             780
cat gtt tta cct tgt cat ctt aag tct tgc ttc ctt tat ttt gga gca    4619
His Val Leu Pro Cys His Leu Lys Ser Cys Phe Leu Tyr Phe Gly Ala
        785             790             795 ttt tta gaa gat aga gtg att gac att tca agg tta ata agg cta tgg    4667
Phe Leu Glu Asp Arg Val Ile Asp Ile Ser Arg Leu Ile Arg Leu Trp
800             805             810             815 ata tca gaa gca ttt ata aaa agt agt gaa ggc agg agg ttg gag gat    4715
Ile Ser Glu Ala Phe Ile Lys Ser Ser Glu Gly Arg Arg Leu Glu Asp
                820             825             830 ata gca gaa ggt tac ttg gag aat ctt att gga aga aat cta gta atg    4763
Ile Ala Glu Gly Tyr Leu Glu Asn Leu Ile Gly Arg Asn Leu Val Met
            835             840             845 gtt act cag agg tcc att tca gat ggt aag gcg aaa gaa tgt cgc ctt    4811
Val Thr Gln Arg Ser Ile Ser Asp Gly Lys Ala Lys Glu Cys Arg Leu
        850             855             860 cat gat gta tta ctc gac ttc tgc aag gaa aga gca gct gag gag aat    4859
His Asp Val Leu Leu Asp Phe Cys Lys Glu Arg Ala Ala Glu Glu Asn
    865             870             875 ttt cta cta tgg ata aat aggtaatatg ataagtaact gtactttcaa           4907
Phe Leu Leu Trp Ile Asn
880             885 tcaatcaagt atttcaagtt atatctgaaa attaatgata tgattttgct aattgatata  4967 ttc agg gat cag att acc aaa cct tct tcc tgt gtt tac tct cac aag    5015
    Arg Asp Gln Ile Thr Lys Pro Ser Ser Cys Val Tyr Ser His Lys
                890             895             900 cag cat gct cac ttg gcc ttc act gaa atg cat aat ctt gta gaa tgg    5063
Gln His Ala His Leu Ala Phe Thr Glu Met His Asn Leu Val Glu Trp
            905             910             915 agt gcg tct tgc tca ttt gtt ggc tcg gta gta ctt tcc aat aaa tat    5111
Ser Ala Ser Cys Ser Phe Val Gly Ser Val Val Leu Ser Asn Lys Tyr
        920             925             930 gac tca tac ttt tcc act cgt gac ata tcc tca cta cat gat ttt tca    5159
Asp Ser Tyr Phe Ser Thr Arg Asp Ile Ser Ser Leu His Asp Phe Ser
    935             940             945 att tca cgc att tta cca aat ttc aag ttt cta aaa gtg tta gat ttg    5207
Ile Ser Arg Ile Leu Pro Asn Phe Lys Phe Leu Lys Val Leu Asp Leu
950             955             960 gaa cac cgg gtt ttt att gat ttt att cca act gag ctt gtt tac ttg    5255
Glu His Arg Val Phe Ile Asp Phe Ile Pro Thr Glu Leu Val Tyr Leu
965             970             975             980 aag tat ttt tct gca cac att gaa cag aat tca att cct tca agc ata   5303
Lys Tyr Phe Ser Ala His Ile Glu Gln Asn Ser Ile Pro Ser Ser Ile
                985             990             995 tcc aat ctt tgg  aac ctt gaa act ctt  ata tta aaa agt cca  ata    5348
Ser Asn Leu Trp  Asn Leu Glu Thr Leu  Ile Leu Lys Ser Pro  Ile
            1000             1005            1010 tat gcg tta cgt tgc acg cta cta cta  cct agt aca gtt tgg  gat    5393
Tyr Ala Leu Arg Cys Thr Leu Leu Leu  Pro Ser Thr Val Trp  Asp
            1015            1020            1025 atg gtt aaa ttg aga cat ctg tat att  cct gac ttc agc aca  agg    5438
Met Val Lys Leu Arg His Leu Tyr Ile  Pro Asp Phe Ser Thr  Arg
            1030            1035            1040 att gaa gca gca tta ctt gag aac tct  gca aaa ctt tat aat  ttg    5483
Ile Glu Ala Ala Leu Leu Glu Asn Ser  Ala Lys Leu Tyr Asn  Leu
            1045            1050            1055 gaa acc ctt tcc act cta tat ttc tct cgt gtt gag gat gca  gaa    5528
Glu Thr Leu Ser Thr Leu Tyr Phe Ser Arg Val Glu Asp Ala  Glu
            1060            1065            1070
```

```
ttg atg ctg aga aaa aca cct aat ctt cga aaa ctg ata tgt gaa      5573
Leu Met Leu Arg Lys Thr Pro Asn Leu Arg Lys Leu Ile Cys Glu
            1075                1080                1085 gtt gaa tgt tta gaa tac ccc cct cag tac cat gtg ttg aat ttt      5618
Val Glu Cys Leu Glu Tyr Pro Pro Gln Tyr His Val Leu Asn Phe
            1090                1095                1100 cca ata cgg ctt gaa ata cta aag ctt tat cga tca aaa ttt aaa      5663
Pro Ile Arg Leu Glu Ile Leu Lys Leu Tyr Arg Ser Lys Phe Lys
            1105                1110                1115 acc atc ccc ttt tgc atc tct gca cca aat ctc aaa tac ttg aaa      5708
Thr Ile Pro Phe Cys Ile Ser Ala Pro Asn Leu Lys Tyr Leu Lys
            1120                1125                1130 ctc tgt ggc ttt tcc ctg gat tct cag tac tta tca gaa act gct      5753
Leu Cys Gly Phe Ser Leu Asp Ser Gln Tyr Leu Ser Glu Thr Ala
            1135                1140                1145 gat cat ctc aag cac ctt gag gta ctc ata ctg tac aag gtt gaa      5798
Asp His Leu Lys His Leu Glu Val Leu Ile Leu Tyr Lys Val Glu
            1150                1155                1160 ttt ggt gat cat agg gaa tgg aaa gtg agc aat ggc aag ttc cct      5843
Phe Gly Asp His Arg Glu Trp Lys Val Ser Asn Gly Lys Phe Pro
            1165                1170                1175 caa ctc aaa atc ttg aaa cta gaa tat ttg tcc ttg gtg aaa tgg      5888
Gln Leu Lys Ile Leu Lys Leu Glu Tyr Leu Ser Leu Val Lys Trp
            1180                1185                1190 att gta gct gat gat gcc ttt cct aac ctt gaa caa ttg gtt ttg      5933
Ile Val Ala Asp Asp Ala Phe Pro Asn Leu Glu Gln Leu Val Leu
            1195                1200                1205 cgt gga tgt caa gat ctt atg gag atc cct tct tgt ttc atg gac      5978
Arg Gly Cys Gln Asp Leu Met Glu Ile Pro Ser Cys Phe Met Asp
            1210                1215                1220 atc ctt tct ctc aag tac atc ggg gta gaa tac tgc aat gag tcg      6023
Ile Leu Ser Leu Lys Tyr Ile Gly Val Glu Tyr Cys Asn Glu Ser
            1225                1230                1235 gtt gtc aag tca gcc ttg aat ata caa gaa aca caa gtc gaa gat      6068
Val Val Lys Ser Ala Leu Asn Ile Gln Glu Thr Gln Val Glu Asp
            1240                1245                1250 tat caa aat act aat ttc aag ctc gtt ctc atc g aggtacacta         6112
Tyr Gln Asn Thr Asn Phe Lys Leu Val Leu Ile
            1255                1260 ctgaaaaaag ctttattctg catgattttg atgaatcaga atcgcctaa attttacaaa  6172 ctgttttctc agttatcttt acctcgtggc ctcgttttac atttgggttc ttctctt   6229 ag ttt tct ttg cag aaa aag gcg tgg aaa tta aat tta act gat       6273
Glu Phe Ser Leu Gln Lys Lys Ala Trp Lys Leu Asn Leu Thr Asp
       1265                1270                1275 gcg gaa gat atg cac aat gca gta aaa aat att ctt gca gaa ata      6318
Ala Glu Asp Met His Asn Ala Val Lys Asn Ile Leu Ala Glu Ile
            1280                1285                1290 aga taggtactac ttttttttt ttcttttcctt ttttaaata caccaaatag         6371
Arg atagattcat cttttttgtc ttttcgatat gaaagggata gaatcagttt catctgatga  6431
gaaagagaag aaacttactg tgaccggaga tgtggatgct gatgaagttc aattagttgt  6491
ggagaaactg agaaagcgtg gcatgccagg gttgtagtcc caacttgtca acacaaatgt  6551
gctatactca ttttgcttac tgtaatacca tttcatgaca cacacacaca aacattaact  6611
gtagtaaagt tttgatggat cagtaaatct gagttcaacc cattgtaatc cgttcaaatt  6671
caactcaaaa aattcccatt gagttattct ttaacagggt atccagagtt tgtagctgga  6731
```

```
gcaatttgga atatcacatg taatttcttt atgagttaat tcgtttaata aaagattctg   6791
taaaacgtcc aacggctgtt gcattcattg taaactaaat atatctcagt atgtaactat   6851
tgaacaaatt tttcatttta gtccctgagg tttgatgtaa gtcattagat tttacggatc   6911
ctgaagtgaa tggttttagc cttttctatt ttcttatgag ttcaccaaaa tgttgtgatg   6971
ccactctgct acatgttaga gaaatgagaa tgttagcacc cgagagtatg gcctagcggt   7031
caatcaatga agcaggtgaa acaacaaaa gcaaaaaata ctaagagatt tcttcacatc   7091
tatctaagta ccgctaagca aagatactgt aatgaccctc ctggtcattt atgtgtcttg   7151
ccttctgtgt gtcgtttaga gtgttcctat agcgaccca agtcatttat gacttgctgg    7211
gactaacggt tcggtcacat ggtcgttcgt ttggttttgg tgcgagtttt tgtgttttgg   7271
agcttatgaa tcttgaacga tgattttcga tcaaaaattc aagaagatga catcggaatc   7331
catttctaac gattccatca gctccggaag ggtcatttta ggctagtagc ttggtcggca   7391
tgactcccgg tgcgattagg ccttttaact ttaagtttaa gcctaagttt gactttggtc   7451
aacattctga gtaaacgcgc tcggatgaga attccgtcag tgcggttagc tccggaatgt   7511
caagtttggt ttagattgac cttttctttg tgtctcgagg ttttttgatat ttttcggagc  7571 tcttttgtgg gttttgactt aaaatggcat ttgggtgtgg aatccacttt ttgtcaagat   7631
gacctcgtat agaaattttg gctgtgccat tgagtccgaa atatcgaatt tgatatgatt   7691
gcatatctcg tttgtgtgca cggggttccg aacgagttcg gagaaccttg tcgcagtttt   7751
taaattttgg ggtaagtgca gaaaaatctg cacttttgga aaaccttaaa aacctcatcc   7811
ctctctcatc cctctctcat ctctcaatca tttaggcgat tcgaagtgtg ggaactttgt   7871 attttgatg gcttcgctgt agagtattca gaagctgttg ggtgcgcgta gttcgaggta   7931
aatttcgtaa aatacctgct gccacgatcc cttttgtgg cttgattttg gaattttga    7991 gatttgtttt cttagccatt tttggtccga tttcagtgat tcttgaggct atcttgagtg   8051 gttttcgag gagagcatcg tggtgttgtc ggaatttact gtagaccacc cattttggt   8111 aaaatatgctg aattaacttc tgtcccattt ctttagtttt tgagaaaaat ttgggttttg   8171
gttgcatgtt ggttatgtgt tgtttttgat ccccgaatgg tgtcccatca tggaacacaa   8231
tttggggagc tgttaagaac ctattttggg ggttaattcc ggagtttcca gcgcgggtcc   8291
cacttctccc gttttgaccc cgaaattgat atgtctccgt ttcttgcgat tttagtgtct   8351
aaacgaccgt aataacattg tgactctatt tttgatagcg gggcagcgtt tcgaggccgt   8411
tcggaaaggg aaagctccgg agaagtgatt tttggagcgt gcgtgatctg cccacaagta   8471
gggtatggtt tccctctctt agattgagct tgagagtgtg aatgcatgtt gattagttgg   8531
gatttgggtt ggtagttatt gaatcatgca taggtgttta gaaatcatgt tttggccttt   8591
tcgggaatta tcgggtaact gtgagcatgc tatgtgttac taattgaccc tccttgctat   8651
gtggagtgct tgaatgcttg attactatt atctgaagca tgttgggcct tagtttaggt    8711
ttgactaggg cttgccttag agatgcatga ttccggatttg ataggcctta gttttgccc   8771 cgacgtcgct cggtcgactt agatccatgt agactggtgt agcaacttga gtctgatagt   8831
ttgggcctta gctaggcgat acgcttgctc cgatgataat tatcttcttc ttctttttt    8891 cgttgttacg gcttcacgag ttacgttggc gacattgatt ctgcttcgcg atttgaagtt   8951
gattttttat tcggttccaa ggacttacat tgattggcta agtgtggacg gcgttccacg   9011
gaaatttata agcatggatc gattgagacc ctttcagcag ctacattggc acttatatag   9071
```

-continued

```
agcatccgat ttaaggtccg gcctctatcg cccaaatact tatatagagc aaccggttta  9131
aggtccggcc tctatcgccc agatacttgt atagagcatc cggttagagg tctggcctca  9191
gttacttgat acttgtgatt ggttacttgg gtacttttgg tgagcatccg gttcgaggtc  9251
cggcctccgt actgtcagat tctactaatt ggggttgaga ttctggttcg atgttttccg  9311
ttcttgggtt cttatatgca atttctttta gttatagtta ttttgtgtac tcatcgggct  9371
tatgggatc cgtttaggtt tttatttaac ttgcgcacga gtgtaccttc tgggcttatg  9431
ggggcccagt taggtgtagt tagcttatag attactttag ttagttcttt ttacacttgt  9491
gtgctttcca tggtttactt agattgtcat tcttgacctc tgtttgtgtt attccttctt  9551
ttcatattgc ctttactttt caagttcagt cggcctataa tgcatactgg gtacctgttg  9611
ttttggtact catgctacgc tctgcatctg tttcgtgatg caggtctgag caccagtggc  9671
cagcgttgat ccagtttgga gtagtctgat ccggagacgg gggtgagcac atggcgtttt  9731
gtactatttc agtctccatc tgtgtatata gacttgtctt ttaccttcg agacagtcca  9791
atctctgtgg tccactttg ggacttgtac tcgttttgtt agtagctctg tactggtgac  9851
ttcctggttc taggagggat ctttatttgt atatatgttt tggttcgctt ccgcctgttt  9911
atattgttat cataaaattt tgcctactct tgttagtttc taccctcaga cccattactt  9971
gttattccgg gttacgggtt ggcttaccta ctggtgggtt atagtatgtg ccaccatgac  10031
tcgagaaatc gggtcgtgac agatacatga tgcctctttg gttggaagaa gcgggtactc  10091
agtcaaatgg tcgaggtgag ctcgacacca tcaataacat cccaaaaaag gaacaatgag  10151
aaagttacaa atcacaatac atgtccatat gctttggaac taaagaattc aaagcacaca  10211
atgtatttca ataatctttt atctctgcct gcagttgaat ataccagata tcagatctga  10271
gacgatgttt aaaaaggaaa ctattattcg accctattcc tttctcaaac ctcgaaacca  10331
acaccagtta tacaacaata tatgcagaac cctttaacta tatactatat acaaatt    10388
```

<210> SEQ ID NO 2
<211> LENGTH: 1293
<212> TYPE: PRT
<213> ORGANISM: Solanum tuberosum

<400> SEQUENCE: 2

```
Met Asn Phe Asn Asn Glu Leu Ser Asp Leu Lys Asn Arg Phe Leu Phe
  1               5                  10                  15

Arg Thr Leu Arg Ala Gln Lys Cys Ser Asp Val Ala Arg Asp Arg Ile
             20                  25                  30

Asp Phe Phe Ile Trp Glu Leu Lys Phe Leu Asn Cys Phe Leu His Leu
         35                  40                  45

Gln Ser Phe Ala Phe Ala Ser Glu Cys Gly Met Leu Asp Ile Ser Gln
     50                  55                  60

Lys Met Ile Glu Ile Cys Lys Arg Phe Asn Thr Pro Pro His Asn
 65                  70                  75                  80

Ser Phe Ala Tyr Trp Lys Glu Val Ile Cys Lys Arg Leu Cys Ala Ile
                 85                  90                  95

Ser Ile Gln Pro Asp Ala Ser Ser Asp Asp Gly Phe Ala Cys Trp Lys
            100                 105                 110

Lys Val Ile Trp Lys Thr Lys Gln Glu Phe Arg Ala Lys Tyr Ser Phe
        115                 120                 125

Pro Lys Thr Leu Leu Ala Asp Asn Lys Val Tyr Asp Asp Asp Thr
    130                 135                 140
```

-continued

```
Asn Pro Lys Phe Val Met Glu Phe Ile Asp Ala Val Val Gly Asn Leu
145                 150                 155                 160

Asn Val Leu Val Lys Ile Asn Asp Pro Ser Ser Leu Leu Phe Val Pro
                165                 170                 175

Gly Pro Lys Glu Gln Ile Glu Gln Val Leu Lys Glu Leu Lys Leu Leu
            180                 185                 190

Arg Phe Phe Val Cys Phe Val Ser Asn Lys Cys Ile Glu Pro Gln Tyr
        195                 200                 205

Gln His Thr Thr Phe Tyr Thr His Ala Leu Ile Glu Ala Ser His Ile
    210                 215                 220

Ala Met Val Val Trp Leu Asn Leu Pro Ile Tyr Gly Asn Arg Asn Gln
225                 230                 235                 240

Asp Leu Ala Ser Ser Glu Val Ser Cys Leu Leu Ser Asp Phe Met Glu
                245                 250                 255

Met Lys Ile Lys Ser Ile Gln Pro Asp Ile Ser Arg Asn Asn Ile Tyr
            260                 265                 270

Ile Asp Val Leu Arg Ala Leu Lys Ser Thr Ile Pro Gln Ala Gln Asp
        275                 280                 285

Lys His Ala Ala Glu Ser Gly Ile Val Glu Thr Pro Thr His Asn Leu
    290                 295                 300

Met Val Gly Leu Ser Asp Gln Met Ala Asn Leu Gln Glu Met Leu Cys
305                 310                 315                 320

Leu Leu Arg Asp Asn Leu Ile His Leu Pro Ile Leu Asp Leu Glu Phe
                325                 330                 335

His Leu Gln Asp Met Asp Ser Val Ile Val Asp Ala Gly Leu Leu Ile
            340                 345                 350

Tyr Ser Leu Tyr Asp Ile Lys Gly Gln Lys Glu Asp Thr Thr Leu Glu
        355                 360                 365

Asp Ile Asn Gln Ala Leu Gly Phe Asp Leu Pro Arg Asn Ile Glu Pro
    370                 375                 380

Ile Lys Ala Met Ile Asn Leu Val Met Gln Lys Ala Phe Gln Cys Asn
385                 390                 395                 400

Leu Pro Arg Ile His Gly Leu Gly Tyr Val Asp Phe Leu Leu Lys Asn
                405                 410                 415

Leu Lys Asp Phe Gln Gly Arg Tyr Ser Asp Ser Leu Asp Phe Leu Lys
            420                 425                 430

Asn Gln Leu Gln Val Ile Gln Thr Glu Phe Glu Ser Leu Gln Pro Phe
        435                 440                 445

Leu Lys Val Val Glu Glu Pro His Asn Lys Leu Lys Thr Leu Asn
    450                 455                 460

Glu Asp Cys Ala Thr Gln Ile Ile Arg Lys Ala Tyr Glu Val Glu Tyr
465                 470                 475                 480

Val Val Asp Ala Cys Ile Asn Lys Glu Val Pro Gln Trp Cys Ile Glu
                485                 490                 495

Arg Trp Leu Leu Asp Ile Ile Glu Glu Ile Thr Cys Ile Lys Ala Lys
            500                 505                 510

Ile Gln Glu Lys Asn Thr Val Glu Asp Thr Met Lys Thr Val Ile Ala
        515                 520                 525

Arg Thr Ser Ser Lys Leu Ala Arg Thr Pro Arg Met Asn Glu Glu Ile
    530                 535                 540

Val Gly Phe Glu Asp Val Ile Glu Asn Leu Arg Lys Lys Leu Leu Asn
545                 550                 555                 560

Gly Thr Lys Gly Gln Asp Val Ile Ser Ile His Gly Met Pro Gly Leu
```

-continued

```
              565                 570                 575
Gly Lys Thr Thr Leu Ala Asn Ser Leu Tyr Ser Asp Arg Ser Val Phe
            580                 585                 590

Ser Gln Phe Asp Ile Cys Ala Gln Cys Cys Val Ser Gln Val Tyr Ser
            595                 600                 605

Tyr Lys Asp Leu Ile Leu Ala Leu Leu Arg Asp Ala Ile Gly Glu Gly
            610                 615                 620

Ser Val Arg Arg Glu Leu His Ala Asn Glu Leu Ala Asp Met Leu Arg
625                 630                 635                 640

Lys Thr Leu Leu Pro Arg Arg Tyr Leu Ile Leu Val Asp Asp Val Trp
                645                 650                 655

Glu Asn Ser Val Trp Asp Asp Leu Arg Gly Cys Phe Pro Asp Val Asn
                660                 665                 670

Asn Arg Ser Arg Ile Ile Leu Thr Thr Arg His His Glu Val Ala Lys
                675                 680                 685

Tyr Ala Ser Val His Ser Asp Pro Leu His Leu Arg Met Phe Asp Glu
            690                 695                 700

Val Glu Ser Trp Lys Leu Leu Glu Lys Lys Val Phe Gly Glu Glu Ser
705                 710                 715                 720

Cys Ser Pro Leu Leu Lys Asn Val Gly Leu Arg Ile Ala Lys Met Cys
                725                 730                 735

Gly Gln Leu Pro Leu Ser Ile Val Leu Val Ala Gly Ile Leu Ser Glu
            740                 745                 750

Met Glu Lys Glu Val Glu Cys Trp Gln Val Ala Asn Asn Leu Gly
            755                 760                 765

Ser Tyr Ile His Asn Asp Ser Arg Ala Ile Val Asp Lys Ser Tyr His
            770                 775                 780

Val Leu Pro Cys His Leu Lys Ser Cys Phe Leu Tyr Phe Gly Ala Phe
785                 790                 795                 800

Leu Glu Asp Arg Val Ile Asp Ile Ser Arg Leu Ile Arg Leu Trp Ile
                805                 810                 815

Ser Glu Ala Phe Ile Lys Ser Ser Glu Gly Arg Arg Leu Glu Asp Ile
            820                 825                 830

Ala Glu Gly Tyr Leu Glu Asn Leu Ile Gly Arg Asn Leu Val Met Val
            835                 840                 845

Thr Gln Arg Ser Ile Ser Asp Gly Lys Ala Lys Glu Cys Arg Leu His
850                 855                 860

Asp Val Leu Leu Asp Phe Cys Lys Glu Arg Ala Ala Glu Glu Asn Phe
865                 870                 875                 880

Leu Leu Trp Ile Asn Arg Asp Gln Ile Thr Lys Pro Ser Ser Cys Val
                885                 890                 895

Tyr Ser His Lys Gln His Ala His Leu Ala Phe Thr Glu Met His Asn
            900                 905                 910

Leu Val Glu Trp Ser Ala Ser Cys Ser Phe Val Gly Ser Val Val Leu
            915                 920                 925

Ser Asn Lys Tyr Asp Ser Tyr Phe Ser Thr Arg Asp Ile Ser Ser Leu
930                 935                 940

His Asp Phe Ser Ile Ser Arg Ile Leu Pro Asn Phe Lys Phe Leu Lys
945                 950                 955                 960

Val Leu Asp Leu Glu His Arg Val Phe Ile Asp Phe Ile Pro Thr Glu
                965                 970                 975

Leu Val Tyr Leu Lys Tyr Phe Ser Ala His Ile Glu Gln Asn Ser Ile
            980                 985                 990
```

-continued

```
Pro Ser Ser Ile Ser Asn Leu Trp  Asn Leu Glu Thr Leu  Ile Leu Lys
        995              1000              1005

Ser Pro  Ile Tyr Ala Leu Arg  Cys Thr Leu Leu  Pro Ser Thr
    1010              1015              1020

Val Trp  Asp Met Val Lys Leu  Arg His Leu Tyr Ile  Pro Asp Phe
    1025              1030              1035

Ser Thr  Arg Ile Glu Ala Ala  Leu Leu Glu Asn Ser  Ala Lys Leu
    1040              1045              1050

Tyr Asn  Leu Glu Thr Leu Ser  Thr Leu Tyr Phe Ser  Arg Val Glu
    1055              1060              1065

Asp Ala  Glu Leu Met Leu Arg  Lys Thr Pro Asn Leu  Arg Lys Leu
    1070              1075              1080

Ile Cys  Glu Val Glu Cys Leu  Glu Tyr Pro Pro Gln  Tyr His Val
    1085              1090              1095

Leu Asn  Phe Pro Ile Arg Leu  Glu Ile Leu Lys Leu  Tyr Arg Ser
    1100              1105              1110

Lys Phe  Lys Thr Ile Pro Phe  Cys Ile Ser Ala Pro  Asn Leu Lys
    1115              1120              1125

Tyr Leu  Lys Leu Cys Gly Phe  Ser Leu Asp Ser Gln  Tyr Leu Ser
    1130              1135              1140

Glu Thr  Ala Asp His Leu Lys  His Leu Glu Val Leu  Ile Leu Tyr
    1145              1150              1155

Lys Val  Glu Phe Gly Asp His  Arg Glu Trp Lys Val  Ser Asn Gly
    1160              1165              1170

Lys Phe  Pro Gln Leu Lys Ile  Leu Lys Leu Glu Tyr  Leu Ser Leu
    1175              1180              1185

Val Lys  Trp Ile Val Ala Asp  Asp Ala Phe Pro Asn  Leu Glu Gln
    1190              1195              1200

Leu Val  Leu Arg Gly Cys Gln  Asp Leu Met Glu Ile  Pro Ser Cys
    1205              1210              1215

Phe Met  Asp Ile Leu Ser Leu  Lys Tyr Ile Gly Val  Glu Tyr Cys
    1220              1225              1230

Asn Glu  Ser Val Val Lys Ser  Ala Leu Asn Ile Gln  Glu Thr Gln
    1235              1240              1245

Val Glu  Asp Tyr Gln Asn Thr  Asn Phe Lys Leu Val  Leu Ile Glu
    1250              1255              1260

Phe Ser  Leu Gln Lys Lys Ala  Trp Lys Leu Asn Leu  Thr Asp Ala
    1265              1270              1275

Glu Asp  Met His Asn Ala Val  Lys Asn Ile Leu Ala  Glu Ile Arg
    1280              1285              1290
```

<210> SEQ ID NO 3
<211> LENGTH: 26
<212> TYPE: DNA
<213> ORGANISM: Artificial sequence
<220> FEATURE:
<223> OTHER INFORMATION: Oligonucleotide

<400> SEQUENCE: 3
aaacccggtg ttccaaatct aacact                                        26

<210> SEQ ID NO 4
<211> LENGTH: 26
<212> TYPE: DNA
<213> ORGANISM: Artificial sequence
<220> FEATURE:

<223> OTHER INFORMATION: Oligonucleotide

<400> SEQUENCE: 4
catgtagtga ggatatgtca cgagtg        26

<210> SEQ ID NO 5
<211> LENGTH: 21
<212> TYPE: DNA
<213> ORGANISM: Artificial sequence
<220> FEATURE:
<223> OTHER INFORMATION: Oligonucleotide

<400> SEQUENCE: 5
attacaatgg gttgaactca g        21

<210> SEQ ID NO 6
<211> LENGTH: 22
<212> TYPE: DNA
<213> ORGANISM: Artificial sequence
<220> FEATURE:
<223> OTHER INFORMATION: Oligonucleotide

<400> SEQUENCE: 6
acctctttca attgttctgg tg        22

<210> SEQ ID NO 7
<211> LENGTH: 22
<212> TYPE: DNA
<213> ORGANISM: Artificial sequence
<220> FEATURE:
<223> OTHER INFORMATION: Oligonucleotide

<400> SEQUENCE: 7
cactcgtgac atatcctcac ta        22

<210> SEQ ID NO 8
<211> LENGTH: 18
<212> TYPE: DNA
<213> ORGANISM: Artificial sequence
<220> FEATURE:
<223> OTHER INFORMATION: Oligonucleotide

<400> SEQUENCE: 8
caaccctggc atgccacg        18

<210> SEQ ID NO 9
<211> LENGTH: 4
<212> TYPE: PRT
<213> ORGANISM: Artificial sequence
<220> FEATURE:
<223> OTHER INFORMATION: Conserved domain

<400> SEQUENCE: 9

Gly Leu Pro Leu
1

<210> SEQ ID NO 10
<211> LENGTH: 4
<212> TYPE: PRT
<213> ORGANISM: Artificial sequence
<220> FEATURE:
<223> OTHER INFORMATION: Conserved domain

<400> SEQUENCE: 10

Gln Leu Pro Leu
1

```
<210> SEQ ID NO 11
<211> LENGTH: 4
<212> TYPE: PRT
<213> ORGANISM: Artificial sequence
<220> FEATURE:
<223> OTHER INFORMATION: Conserved domain

<400> SEQUENCE: 11

Cys Lys Leu Tyr
1

<210> SEQ ID NO 12
<211> LENGTH: 4
<212> TYPE: PRT
<213> ORGANISM: Artificial sequence
<220> FEATURE:
<223> OTHER INFORMATION: Conserved domain

<400> SEQUENCE: 12

Cys Phe Leu Tyr
1
```

US 7,435,874 B2

PLANT RESISTANCE GENE

This application is the United States national stage of International Application No. PCT/EP02/09738, filed Aug. 30, 2002, which was published under PCT Article 21(2) in English as International Publication No. WO 03/020013, and which claims benefit of European patent application Ser. No. 01120670.3 filed Aug. 31, 2001.

BACKGROUND OF THE INVENTION

1. Field of the Invention

The present invention relates to the R1 resistance gene from potato. It further relates to methods and materials employing the gene, and processes for identifying or producing other related genes. It also relates generally to methods for identifying plant protective agents which are capable of inducing the R1 gene or the activity of its encoded protein. Furthermore, the present invention relates to transgenic plants which became resistant to Late Blight because of the expression of an R1 transgene.

2. Description of Related Art

Several documents are cited throughout the text of this specification by name. Full bibliographic citations may be found at the end of the specification immediately preceding the sequence listing or claims. Each of the documents cited herein (including any manufacturer's specifications, instructions, etc.) are hereby incorporated herein by reference; however, there is no admission that any document cited is indeed prior art as to the present invention.

Late blight is worldwide the most destructive disease for potato cultivation causing billion-dollar losses every year (Kamoun et al. 1999). The causal pathogen is *Phytophthora infestans*, an oomycetous fungus infecting also tomatoes (Judelson 1997). Complete destruction of the potato crop by late blight caused the "Irish potato famine" in the middle of the 19$^{th}$ century (Salaman 1985) and initiated the search for resistant plants. Single genes for resistance to late blight (R genes) were discovered nearly 100 years ago in *S. demissum*, a wild potato species indigenous to Mexico. Introgression into potato cultivars of R genes conferring race specific resistance provided, however, only transient resistance to late blight, as new races rapidly overcame the R gene mediated resistance (Wastie 1991, Fry and Goodwin 1997). Quantitative or field resistance to late blight has also been identified in wild potato species (Ross 1986). This resistance is more durable than the one mediated by R genes, but difficult to move into cultivated varieties by crossing and phenotypic selection. Late blight is still mostly controlled by the frequent application of fungicides which loose efficiency by selection of fungicide resistant isolates.

Several R genes have been mapped to potato chromosomes using DNA markers (Leonards-Schippers et al. 1992, El-Kharbotly et al. 1994, 1996, Li et al. 1998, Ewing et al. 2000, Naess et al. 2000). R1 is located on chromosome V (Leonards-Schippers et. al., 1992) in a region where single genes for resistance to Potato virus X have also been mapped (Ritter et al. 1991, De Jong 1997). The same region contains major quantitative trait loci (QTL) for resistance to the parasitic root cyst nematode *Globodera pallida* (Kreike et al. 1994, Rouppe van der Voort et al. 1997, 2000) and late blight (Leonards-Schippers et. al. 1994, Oberhagemann et al. 1999, Collins 1999). The presence of a hot spot of resistance genes suggests their evolution from common ancestors by local gene duplication followed by functional diversification (Leonards-Schippers et al. 1994, Leister et al. 1996, Oberhagemann et al. 1999, Gebhardt and Valkonen 2001). If this is the case, the molecular cloning of the R1 gene should open the possibility to study at the molecular cloning factors mapping to the region and participating to the control of qualitative and quantitative resistance to various pathogens.

Thus, the technical problem underlying the present invention was to comply with the need for plant pathogen resistance genes and their regulatory sequences.

The solution to the technical problem is achieved by providing the embodiments characterized if the claims and described further below.

BRIEF SUMMARY OF THE INVENTION

In accordance with the present invention R1, the first gene for resistance to Late blight has been cloned and characterized at the molecular level. The gene was identified by a particular combined positional cloning and candidate gene approach. The molecular structure of the gene allows to classify R1 among plant resistance genes containing conserved NBS-LRR and leucine-zipper motifs (Ellis et al. 2000, Dangl and Jones, 2001).

R1 was cloned by using a positional cloning strategy in combination with searching for candidate genes having DNA sequence similarity to known plant resistance genes (Hammond-Kosack and Jones 1997, Ellis et al. 2000). A similar approach was successful for cloning potato genes for resistance to Potato Virus X (Rx1, Bendahmane et al. 1999) and the root cyst nematode *Globodera pallida* (Gpa2, Van der Vossen et al. 2000). A chromosome walk towards R1 was initiated from two marker loci SPUD237 and AFLP1, flanking R1 at short genetic distances of 0.1 cM. Walking from marker AFLP1 proved unproductive, however, due to scarcity of BAC and YAC clones (Leister et al. 1997) having the AFLP1 marker. The identification of potato genomic clones with overlapping inserts was facilitated by BAC technology in combination with the use of macroarrays of BAC clones. Application of this approach was successful in rice (Nakamura et al. 1997, Yang et al. 1997, Yang et al. 1998) and tomato (Folkertsma et al. 1998). The physical map (FIG. 1) covers at least 250 kb of the potato genome. Around 200 kb were a candidate region for containing the R1 gene based on linkage without recombination to BAC end markers. The candidate region was open-ended towards the AFLP1 locus because the single recombination event separating R1 and AFLP1 was not included in the physical map. Partial sequence information from the candidate region identified an RGL resistance-gene like gene fragment that detected a gene family with members present on both chromosomes carrying the susceptibility allele r1 or the resistance allele R1. In fact, the RGL probe used to identify cDNA and BAC clones for R1 was part of an r1 susceptibility allele. Based on an allele specific PCR assay derived from a cDNA clone encoding part of R1, a functional member of the candidate gene family was shown to be present in plants having the R1 resistance allele and to be absent in susceptible plants. This candidate gene was subcloned from BAC BA87d17 and stably transformed into the susceptible cultivar Desirée. Complementation of the R1 phenotype in several transgenic plants showed that the candidate gene was, indeed, the R1 gene.

Accordingly, the present invention relates to a nucleic acid molecule encoding a polypeptide which is capable of conferring resistance against a pathogen in a plant in which said polypeptide is expressed, said nucleic acid molecule comprising or consisting of a nucleotide sequence selected form the group consisting of:

(a) a nucleotide sequence encoding at least the mature form of a protein (R1) comprising the amino acid sequence as given in SEQ ID NO: 2;
(b) a nucleo ide sequence comprising at least one or more coding regions of the DNA sequence as given in SEQ ID NO: 1,
(c) a nucleotide sequence hybridizing with the complementary strand of a nucleotide sequence as defined in (a) or (b) under stringent hybridization conditions;
(d) a nucleotide sequence encoding a protein derived from the protein encoded by a nucleotide sequence of (a) or (b) by way or substitution, deletion and/or addition of one or several amino acids of the amino acid sequence encoded by the nucleotide sequence of (a) or (b);
(e) a nucleotide sequence encoding a protein having a amino acid sequence at least 60% identical to the amino acid sequence encoded by the nucleotide sequence of (a) or (b);
(f) a nucleotide sequence encoding at least a Leucine zipper (Z) domain corresponding to amino acid portion 308-329 of SEQ ID NO: 2, a nucleic binding site (NBS) domain corresponding to amino acid position 572-682 of SEQ ID NO: 2 and/or a Leucine rich repeat (LRR) domain corresponding to amino acid position 780-1280 of SEQ ID NO: 2;
(g) a nucleotide sequence encoding an epitope-bearing portion of a R1 protein encoded by a nucleotide sequence of (a) or (b);
(h) a nucleotide sequence comprising at least 15 consecutive nucleotides of a nucleotide sequence of any one of (a) to (g);
(i) nucleotide sequence encoding a polypeptide comprising a one or more motifs as given in the SEQ ID NOs: 10 and 12, in FIG. 4 or the amino acid sequence LHD;
(j) DNA sequences obtainable by screening an appropriate library under stringent conditions with a probe having at least 17 consecutive nucleotides of a nucleotide sequence of any one of SEQ ID NOS: 1 or 5 to 8;
(k) a nucleotide sequence encoding fragment of at least 6 consecutive amino acids of a protein encoded by a nucleotide sequence of (a) or (b); and
(l) the nucleotide sequence of which is degenerate as a result of the genetic code to a nucleotide sequence of any one of (a) to (i).

According to a first aspect of the present invention there is provided a nucleic acid molecule encoding a polypeptide which is capable of conferring resistance against a pathogen, such as fungi, in a plant into which said polypeptide is expressed.

Nucleic acid molecules according to the present invention may be provided in recombinant form or free or substantially free of nucleic acid or genes of the species of interest or origin other than the sequence encoding a polypeptide with the required function. The nucleic acid molecules (and their encoded polypeptide products) may also be (i) isolated and/or purified from their natural environment (although not necessarily in pure form per se), or (ii) in substantially pure or homogeneous form.

Nucleic acid according to the present invention may include cDNA, RNA, genomic DNA, preferably the intact gene, and may be wholly or partially synthetic (constructs'). Where a DNA sequence is specified, e.g. with reference to a figure or SEQ ID NO, unless context requires otherwise the RNA equivalent, with U substituted for T where it occurs, is encompassed. Also encompassed is the complement of the various disclosed sequences, which may be used in probing experiments, or in down-regulation of the sequence.

A particular aspect of the invention is a nucleic acid molecule having the sequence all or part of the sequence shown in SEQ ID NO: 1 including (where appropriate) both coding and/or non-coding regions. Within SEQ ID NO: 1 there is apparently a large open reading frame (ORF). Subsequent comparison of the genomic DNA sequence with the sequence of cDNAs revealed that the gene contains three exons and three introns; see Example 5 and FIG. 4. The putative R1 polypeptide sequence is shown in FIG. 4 designated SEQ ID NO: 2. R1 appears to contain 1293 amino acid residues and has a molecular weight of 149.4 kDa. Particular nucleic acid molecules of this aspect of the invention include those encoding the R1 protein product and cDNA, believed to be base 2223-6321 excluding the introns marked as shown (4878-4970 and 6130-6229 inclusive). Surprisingly the primary structure of R1 is similar to that of the L. ZipI NBS-LRR (Hammond-Kosack and Jones 1997) class of R proteins. Based on the deduced protein sequence, R1 belongs to the L.Zip/NBS/LRR class of plant resistance genes (Hammond-Kosack and Jones 1997). The leucine zipper motif (L.Zip) in the amino-terminal region is thought to feature in dimerization or interaction with other proteins. The downstream putative nucleotide-binding site (NBS) domain may be involved in the signal transduction pathway leading to the onset of the resistance response. The C-terminal leucine-rich repeat (LRR) domain matches the consensus sequence for a cytoplasmic LRR domain as described by Jones and Jones (1997) and may function in protein-protein interactions and ligand binding. It has been shown that the LRR domains of alleles of the flax rust resistance gene L determine recognition of specific races of the pathogen (Ellis et al. 1999). Prediction in silico of four myristylation and 43 phosphorylation sites in the R1 sequence suggests a possible anchoring of the R1 protein in the plasma membrane and phosphorylation/dephosphorylation steps, respectively, participating in signal transduction (Dangl and Jones 2001).

R1 is located on the short arm of chromosome V (Leonards-Schippers et al. 1992, Dong et al. 2000) and is sequence related to the tomato Prf gene for resistance to *Pseudomonas syringae* that is located on tomato chromosome 5 within the Pto/Fen resistance gene cluster (Salmeron et al. 1996). Chromosomes five of potato and tomato are colinear with each other except a paracentric inversion of the short arm (Tanksley et al. 1992). The potato locus StPto corresponding to Pto/Fen maps more than 10 cM proximal to R1 (Leister et al. 1996), excluding, therefore, the possibility that R1 and Prf are located in a colinear genomic region. This is the case, however, when considering the tomato Bs4 gene conferring resistance to the bacterial pathogen *Xanthomonas campestris*. The position of the potato locus corresponding to Bs4 can be inferred from the tight linkage (1 cM) between Bs4 and the marker TG432 (Balivora et al. 2001) which maps 3.8 cM distal to GP21 on the tomato molecular map (Tanksley et al. 1992). This region of the tomato chromosome 5 that extends distal from the GP21 marker should be colinear with the potato interval GP21-GP179 including R1, when taking into account the paracentric inversion between the two genomes.

Two potato genes for resistance to Potato Virus X, Rx2 and Nb, also map to similar positions as R1 (Ritter et al. 1991, Leonards-Schippers et al. 1992, De Jong et al. 1997). The Rx2 gene has been cloned and is, like R1, a member of the L.Zip/NBS/LRR class of resistance genes (Bendahmane et al. 2000). The two resistance genes share only 32% sequence identity and are, therefore, rather different members of the same superfamily of genes. Nb is located in the interval GP21-SPUD237 (De Jong et al. 1997) not containing R1 and is genetically separated, therefore, from R1.

In a further aspect of the invention there are disclosed active, homologous, variants of the R1 sequences, which may for instance be mutants or other derivatives, or naturally occurring R1 homologues such as allelic variants, paralogues (from the same species, but at a different location e.g. pseudoalleles at linked loci), or orthologues (related genes from different species). Examples of these are shown below. In each case the variant encodes a product which is homologous (similar) to R1, which may be isolated or produced on the basis of that sequence, and is capable of conferring pathogen resistance against one or more pathogens.

Resistance gene activity can be tested by conventional methods known in the art, as appropriate to the nature of the resistance being investigated. Example methods can be found in the following publications: bacterial (Grant, (1995) Science 269, 843-846); fungal (Dixon, (1996) Cell 84, 451-459; Jones, (1994) Science 266, 789-793; Thomas, (1997) The Plant Cell 9, 2209-2224; nematode and viral (Whitham, (1994) Cell 78, 1101-1115). Typically, activity is tested by complementation of trait in a plant; see example 4. This can be achieved by using the isolated gene or for example by coupling the putative active variant to a promoter and terminator for expression in plants and transforming it into a susceptible plant that lacks a given resistance trait. The activity of the R1 variant is then confirmed by challenge with the appropriate pathogen. Alternatively a transient expression assay can be used to test for activation of the R1 variant analogous to the assay used by Mindrinos, (1994) Cell 78, 1089-1099. Briefly, the putative active R1 variant is coexpressed from a plasmid with a pathogen-derived gene which is an elicitor of the resistance specified by the putative.

R1 homologue, and a reporter gene (e.g. GUS). If the variant is activated by the continuous expression of the pathogen derived gene, then an HR would result and the reporter gene activity would be abolished. If no activity was initiated, then the reporter gene would be detectable.

Similarity or homology between the variant and R1 may be as defined and determined by the TBLASTN program, of Altschul, (1990) J. Mol. Biol. 215, 403-10, which is in standard use in the art, or, and this may be preferred, the standard program BestFit, which is part of the Wisconsin Package, Version 10, January 1999, (Genetics Computer Group, 575 Science Drive, Madison, Wis., USA, Wisconsin 53711), which has been used to calculate sequence homologies in the present application. DNASTAR software using the CLUSTAL method with PAM250 residue weight table (gap penalty 10, gap length 10) may also be used. Homology (or similarity, or identity) may be at the nucleotide sequence and/or the expressed amino acid sequence level. Preferably, the nucleic acid and/or amino acid sequence shares homology with the coding sequence or the sequence encoded by the nucleotide sequence of SEQ ID NO:1 or other sequences set out herein, preferably at least about 50%, or 60%, or 70%, or 80% homology, most preferably at least about 90%, 95%, 96%, 97%, 98% or 99% homology. Homology may be over the full-length of the relevant sequence shown herein, or may more preferably be over a contiguous sequence of about or greater than about e.g. 20, 100, 200, 300, 500, 600 or more amino acids or codons, compared with the relevant amino acid sequence or nucleotide sequence as the case may be.

There are believed to be more than two homologues of R1 in the potato genome. It is likely that one or more of these homologues are R genes against viruses, fungi, bacteria or nematodes.

Naturally occurring R1 variants may be isolated, in the light of the present disclosure, without burden from any suitable plant. Naturally occurring R1 variants may be isolated, from e.g. genomic or cDNA. The putative resistance genes can be obtained using materials (e. g. primers or probes) based on regions peculiar to R1, for instance designated in FIG. 4 (SEO ID NO: 2). As discussed in the appended examples, the R1 gene identified according to the present invention in potato is expected to define a novel class of plant resistance genes. Corresponding genes encoding proteins displaying similar properties should therefore be present in other plants as well. Nucleic acid molecules of the invention can be obtained, e.g., by hybridization of the above-described nucleic acid molecules with a (sample of) nucleic acid molecule(s) of any source. Nucleic acid molecules hybridizing with the above-described nucleic acid molecules can in general be derived from any plant possessing such molecules, preferably form dicotyledonous plants, in particular from any plant of interest in agriculture, horticulture or wood culture, such as crop plants, namely those of the family Solanaceae, such as potato and tomato but also from plants such as manioc, leguminous plants, oil producing plants, such as oilseed rape, linenseed, etc., plants using polypeptide as storage substances, such as soybean, plants using sucrose as storage substance, such as sugar beet or sugar cane, trees, ornamental plants as well as plants that can be used for the production of biomass, regenerative energy, or building materials such as cambric grass etc.

Thus a further aspect of the present invention provides a method of identifying and/or cloning homologous R1 genes from a plant, which method employs all or part of a nucleotide sequences as described above. Thus in one embodiment, nucleotide sequence information provided herein may be used in a data-base (e.g. of ESTs, or STSs, or other genomic sequence information) search to find homologous sequences, expression products of which can be tested for pathogen resistance activity e.g. using methods based on the transient assays of the present invention, or conventional phenotype assays in transgenic plants.

Alternatively, probes based on the sequence may be used e.g. in southern blotting. For instance DNA may be extracted from cells taken from plants displaying the appropriate resistance trait and digested with different restriction enzymes. Restriction fragments may then be separated (e.g. by electrophoresis on an agarose gel) before denaturation and transferred to a nitrocellulose filter. Labelled probe may be hybridised to the DNA fragments on the filter and binding determined.

Preliminary experiments may be performed by hybridising under low stringency conditions. For probing, preferred conditions are those which are stringent enough for there to be a simple pattern with a small number of hybridisations identified as positive which can be investigated further. For example, hybridizations may be performed using a hybridization solution comprising: 5×SSC (wherein SSC=0.15 M sodium chloride; 0.15 M sodium citrate; pH 7), 5× Denhardt's reagent, 0.5-1.0% SDS 100 μg/ml denatured, fragmented salmon sperm DNA, 0.05% sodium pyrophosphate and up to 50% formamide. Hybridization is carried out at 37-42° C. for at least six hours. Following hybridization, filters are, washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989): Tm=81.5° C.+16.6Log [Na+]+0.41 (% G+C)−0.63 (% formamide)−600/#bp in duplex. As an illustration of the above formula, using [Na+]=[0.368] and 50-% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42 C. Such a sequence would be considered substantially homologous to the nucleic acid sequence of the present invention. It is well known in the art to increase stringency of hybridisation gradually until only a few positive clones remain. Other suitable conditions include, e.g. for detection of sequences that are about 80-90% identical, hybridization overnight at 42° C. in 0.25M, Na2HPO4, pH 7.2, 6.5% SDS, 10%, dextran sulfate and, a final wash at 55 C. in 0.1×SSC; 0.1% SDS. For detection of sequences that are greater than about 90% identical, suitable conditions include hybridization overnight at 65° C. in 0.25M, Na2HPO4, pH 7.2, 6.5% SDS, 10% dextran sulfate and a final wash at 60° C. in 0.1×SSC, 0.1% SDS.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include amplification using PCR (including, where appropriate, RACE PCR), RN'ase protection and allele specific oligonucleotide probing.

The identification of successful hybridisation is followed by isolation of the nucleic acid which has hybridised, which may involve one or more steps of PCR or amplification by cloning in a vector that replicates in a suitable host.

In each case, if need be clones (e.g. lambda, cosmid, plasmid, BACs, biBACS) or fragments identified in the search can be extended or supplemented. For instance if it is suspected that they are incomplete, the original DNA source (e.g. a clone library, mRNA preparation etc.) can be revisited to isolate missing portions e.g. using sequences, probes or primers based on that portion which has already been obtained to identify other clones containing overlapping sequence (see e.g. "Principles of Genome Analysis" by S B Primrose (1995) Pub. Blackwell Science Ltd, Oxford, UK).

The nucleic acid molecules or corresponding genes can then be tested for functionality, for example, as described in the examples. One scheme for isolating R1 homologues is as follows:

I) produce a population in which a resistance trait is segregating.
II) PCR amplify DNA from individual members of the population with primers based on the sequence of R1 (but not from the R gene conserved motifs).
III) test the PCR products (either by direct sequence analysis or restriction enzyme digestion) for sequence polymorphism that cosegregates with the R trait. Identify an appropriate polymorphic marker sequence.
IV) Isolate the complete coding sequence of the polymorphic gene. This could be done from an appropriate cloned library or by amplifying it using primers from the 5' and 3' extremes of R1. In each case the identified polymorphic PCR product, or sequence information provided by it, is used to identify the gene.

Resistance gene coding activity can then be tested as described above or in the examples.

A more specific approach is based on the understanding that homologous R1-genes may be linked in clusters. Clustering of R-genes in potato has already been reported (Leister et al. 1996; De Jong et al. 1997). One of the large R-gene clusters is on the short arm of potato chromosome V.

The resistance hot spot on potato chromosome V which includes R1, also contains major QTL (Quantitaive Trait Loci) for resistance to *Phytophthora infestans* (Leonards-Schippers et al. 1994, Oberhagemann et al. 1999, Collins et al. 1999) and the root cyst nematode *Globodera pallida* (Kreike et al. 1994, Rouppe van der Voort et al. 1997, 2000). Linkage disequilibrium mapping revealed strong association between markers in the 0.8 cM interval SPUD237-GP179 containing R1 and resistance of foliage and tubers to late blight supporting tight linkage between R1 and the factors controlling quantitative resistance to late blight. It has been suggested, based on the observed genetic linkage, that R1 and the factors controlling quantitative resistance to late blight may be alleles of the same gene or members of a clustered gene family (Leonards-Schippers et al. 1994, Oberhagemann et al. 1999). The first molecular analysis of the R1 locus now revealed that the latter option is more favourable as R1 is a member of a gene family and is present as an extra copy in a DNA insertion in the R1 bearing chromosome. A similar finding has been reported for the Rpm1 locus in *Arabidopsis* (Stahl et al. 1999). The R1 gene should have been introgressed into the *S. tuberosum* genome from the wild species *S. demissum* through heterogeneous chromosomal crossing over. In crosses between wild and cultivated *Solanum* species heterogenetic chromosome pairing is frequently found (Singh et al. 1989). A second highly homologous member of the R1 gene family, having two alleles r1.1 and r1.2, is located physically close to R1. Further studies on the functionality of this gene are required. With the R1 sequence being available, other members of the R1 family can now be identified that might be present in those parts of the GP21-GP179-interval not yet covered by the physical map and/or in other parts of the potato genome. Allelic variants in *S. tuberosum* and homologs in other Solanaceae species may be isolated which are involved in quantitative resistance to *P. infestans*.

It is thus a preferred embodiment of the present invention that said pathogen which a plant expressing a nucleic acid molecule of the invention is resistant against is *Phythophthora infestans*.

The interaction between R1 and the late blight pathogen is in concordance with the gene-for-gene concept (Person et al. 1962, Flor 1971). Transfer of a single gene was sufficient to elicit in a susceptible host plant the hypersensitive resistance response upon infection with a *P. infestans* race carrying the avirulence gene Avr1 (all races except those with race 1 specificity). Avr1 segregates as single dominant factor in offspring of *P. infestans* strains heterozygous for Avr1 and was mapped to linkage group IV of the *P. infestans* molecular map (Van der Lee et al. 2001). No avirulence factor of *P. infestans* has been cloned so far. Further characterization of R1 at the molecular level and cloning of the Avr1 gene should contribute to clarify how the resistance protein recognises the avirulence effector molecule. Cloning of late blight resistance genes that recognise avirulence factors different from Avr1 might allow identification of the molecular motifs that determine the specificity of effector recognition and may help to engineer R-proteins with broader and more durable resistance to late blight. Other, linked, R1 variants (providing different R traits) may be isolated essentially as set out above, but wherein the DNA used for the initial amplification step is taken from members of the population in which the required R trait co-segregates with R1 itself (or an R1 variant).

It has been noted by the present inventors that the sequence of R1 is similar to the sequence of the otherwise unrelated Prf gene that confers resistance in tomato against a bacterial pathogen, i.e. *P. syringae* (Salmeron et al. 1996). In the light of this information it appears that the sequence of R1 could be modified e.g. by site directed or random mutation, to produce R1 mutants or other derivatives which can confer resistance against (i.e. is switched on by) pathogens that are quite different from *P. infestans*. This can be achieved as described below, with R1 mutants being tested with the transient expression assay methods described above.

Preferably the nucleic acid molecule which is the mutant or other derivative is generated either directly or indirectly (e.g. via one or amplification or replication steps) from an original nucleic acid corresponding to all or part of the sequence shown in SEQ ID NO:1 or other sequences disclosed, herein.

Thus a further aspect of the present invention is a method of producing a nucleic acid encoding an R1 derivative comprising the step of modifying a nucleic acid molecule encoding R1. The derivative may include changes to the nucleic acid molecule which make no difference to the encoded amino acid sequence (i.e. degeneratively equivalent). Changes to a sequence, to produce a mutant or derivative, may be by one or more of addition, insertion, deletion or substitution of one or more nucleotides in the nucleic acid, leading to the addition, insertion, deletion or substitution of one or more amino acids in the encoded polypeptide. In addition to one or more changes within the R1 sequence, a variant nucleic acid may encode an amino acid sequence including additional amino acids at the C-terminus and/or N-terminus.

Specifically included are parts or fragments (however produced) corresponding to portions of the sequences provided, and which encode polypeptides having biological activity, for instance pathogen resistance or the ability to raise or bind R1-binding antibodies.

Generally speaking, changes may be desirable for a number of reasons, including introducing or removing the following features: restriction endonuclease sequences; codon usage; other sites which are required for post translation modification; cleavage sites in the encoded polypeptide; motifs in the encoded polypeptide for glycosylation, lipoylation etc. Leader or other targeting sequences may be added to the expressed protein to determine its location following expression. All of these may assist in efficiently cloning and expressing an active polypeptide in recombinant form (as described below). Preferred modifications include those which decreases the net negative charge of the region in or around QLPL, CFLY or LHD motifs. Means and methods how to modify resistant genes are known to the person skilled in the art and described, for example in WO 01/29239 for the Rx gene of *Solanum tuberosum*. Other desirable mutation may be random or site directed mutagenesis in order to alter the activity (e.g. specificity) or stability of the encoded polypeptide.

As is well-understood, homology at the amino acid level is determined in terms of amino acid similarity or identity. Similarity allows for conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation.

Also included are homologues having non-conservative substitutions. As is well known to those skilled in the art, substitutions to regions of a peptide which are not critical in determining its conformation may not greatly affect its activity because they do not greatly alter the peptide's three dimensional structure. In regions which are critical in determining the peptides conformation or activity such changes may alter the properties of the polypeptide. Indeed, changes such as those described above may confer slightly advantageous properties on the peptide e.g. altered stability or specificity, in particular broader specificity.

Mutants having these properties can then be selected as described above.

Other methods may include mixing or incorporating sequences from related resistance genes into the R1 sequence. For example restriction enzyme fragments of R1 could be ligated together with fragments of an R1 homologue or even of an unrelated gene to generate recombinant versions of R1. An alternative strategy for modifying R1 would employ PCR as described above (Ho et ail., 1989 Gene 77, 51-59) or DNA shuffling (Crameri et al., 1998 Nature 391).

Thus the methods of the invention, described above, may include hybridisation of one or more (e.g. two) probes or primers based on the R1 sequence either to screen for R1 homologues or to produce R1 derivatives. Such, oligonucleotides, probes or primers form a further part of the present invention. An oligonucleotide for use in probing or PCR may be about 30 or fewer nucleotides in length (e.g. 18, 21 or 24). Generally specific primers are upwards of 14 or 15 nucleotides in length. For optimum specificity and cost effectiveness, primers of 16-24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

In one aspect of the present invention, the nucleic acid molecule described above is in the form of a recombinant and preferably replicable vector.

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eucaryotic (e.g. higher plant, mammalian, yeast or fungal cells).

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

By "promoter" is meant a sequence of nucleotides from which transcription may be initiated of DNA operably linked downstream (i.e. in the 3-direction on the sense strand of double-stranded DNA).

"Operably linked-means joined as part of the same nucleic acid molecule, suitably positioned and oriented for transcription to be initiated from the promoter. DNA operably linked to a promoter is "under transcriptional initiation regulation" of the promoter.

Thus this aspect of the invention provides a gene construct, preferably a replicable vector, comprising a promoter operatively linked to a nucleotide sequence provided by the present invention, such as the coding region of the R1 gene, or a variant (e.g mutant, derivative or allele) thereof. Generally speaking, those skilled in the art are well able to construct vectors and design protocols for recombinant gene expression. Suitable vectors can be chosen or constructed containing appropriate regulatory sequences, including promoter sequences, terminator fragments, polyadenylation sequences, enhancer sequences, marker genes and other sequences as appropriate. For further details see for example, Molecular Cloning: a Laboratory Manual: 2nd edition, Sambrook et al, 1989, Cold Spring Harbor Laboratory Press. Many known techniques and protocols for manipulation of nucleic acid, for example in preparation of nucleic acid constructs, mutagenesis (see above), sequencing, introduction of DNA into cells and gene expression, and analysis of proteins, are described in detail in Current Protocols in Molecular Biology, Second Edition, Ausubel et al. eds., John Wiley & Sons, 1992. The disclosures of Sambrook et al. and Ausubel et al. are incorporated herein by reference.

In one embodiment of this aspect of the present invention provides a gene construct, preferably a replicable vector, comprising an inducible promoter operatively linked to a nucleotide sequence provided by the present invention.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

Possible regulatory elements permitting expression in prokaryotic host cells comprise, e.g., the $P_L$, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma Virus), CMV-enhancer, SV40-enhancer or a globin intron in mammalian and other animal cells. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL).

Particularly of interest in the present context are plant vectors. Specific procedures and vectors previously used with wide success upon plants are described by Bevan (Nucl. Acids Res. 12,8711-8721 (1984)) and Guerineau and Mullineaux (1993) (Plant transformation and expression vectors. In: Plant Molecular Biology Labfax (Croy RRD ed) Oxford, BIOS Scientific Publishers, pp 121-148). Suitable promoters which operate in plants include the Cauliflower Mosaic Virus 35S (CaMV 35S) gene promoter that is expressed at a high level in virtually all plant tissues (Benfey et al, 1990a and 1990b); the cauliflower meri 5 promoter that is expressed in the vegetative apical meristem as well as several well localised positions in the plant body, e.g. inner phloem, flower primordial branching points in root and shoot (Medford, 1992; Medford et al, 1991) and the *Arabidopsis thaliana* LEAFY promoter that is expressed very early in flower development (Weigel et al, 1992). Other promoters include the rice actin promoter.

The promoter may include one or more sequence motifs or elements conferring developmental and/or tissue-specific regulatory control of expression.

Thus the vectors of the present invention may-include the R1 gene or a variant thereof, in addition to various sequences required to give them replicative, integrative and/or expression functionality. Such vectors can be used, for instance, to make plants into which they are introduced resistant to *P. infestans* or other fungi.

If it is desired to induce broader-spectrum resistance, various further options are available in the light of the present disclosure:

(a) Modify the R1 sequence, to produce mutants or other derivatives as discussed above, such that its effect can be initiated by elicitors or pathogens other than *P. infestans* alone or the other natural elicitors discussed herein.

(b) Co-express R1 directly with an appropriate elicitor (e.g. Avr 1 from an avirulent strain).

(c) Co-express R1 and an elicitor gene, the transcription or translation of which is suppressed by the activation of R1. This would recouple R1 to its elicitor, and better mimic the natural response to *P. infestans* infection which results in broad specificity silencing.

(d) Co-express R1 with an elicitor gene, the translation of which is only switched on in the presence of pathogen (s).

(e) Co-express R1 with an elicitor gene, whereby one or both are inactivated, and reactivate the gene (s) in a variegated manner, such that the HR is limited only to certain sectors of the plant (e.g. somatically defined sectors) but whereas the defensive response extends beyond these sectors. This could be achieved, for instance, by analogy with the methods disclosed in WO95/31564, wherein, following a backcross between a plant carrying a transposon tagged resistance gene (in that case cf-9) plus intact elicitor (Avr-9) and a plant carrying an activator transposase, the progeny exhibited a somatic reactivation of the cf-9, leading to a localised necrotic response but widespread resistance.

In addition to the vectors and constructs above, the present invention also provides methods comprising introduction of the R1 constructs discussed above, (such as vectors) into a host cell and/or induction of expression of a construct within a plant cell, by application of a suitable stimulus, an effective exogenous inducer. The vectors described above may be introduced into hosts by any appropriate method e.g. conjugation, mobilisation, transformation, transfection, transduction or electroporation, as described in further detail below.

In a further aspect of the invention, there is disclosed a host cell containing nucleic acid or a vector according to the present invention, especially a plant or a microbial cell. The host cell can be any prokaryotic or eukaryotic cell, such as bacterial, insect, fungal, plant or animal cells. Preferred fungal cells are, for example, those of the genus *Saccharomyces*, in particular those of the species *S. cerevisiae*.

For the expression of the nucleic acid molecules according to the invention in sense or antisense orientation in plant cells, the molecules are placed under the control of regulatory elements which ensure the expression in plant cells. These regulatory elements may be heterologous or homologous with respect to the nucleic acid molecule to be expressed as well with respect to the plant species to be transformed. In general, such regulatory elements comprise a promoter active in plant cells. To obtain expression in all tissues of a transgenic plant, preferably constitutive promoters are used, such as the 35 S promoter of CaMV (Odell, Nature 313 (1985), 810-812) or promoters of the polyubiquitin genes of maize (Christensen, Plant Mol. Biol. 18 (1982), 675-689). In order to achieve expression in specific tissues of a transgenic plant it is possible to use tissue specific promoters (see, e.g., Stockhaus, EMBO J. 8 (1989), 2245-2251). Known are also promoters which are specifically active in tubers of potatoes or in seeds of different plants species, such as maize, *Vicia*, wheat, barley etc. Inducible promoters may be used in order to be able to exactly control expression. An example for inducible promoters are the promoters of genes encoding heat shock proteins. Also microspore-specific regulatory elements and their uses have been described (WO96/16182). Furthermore, the chemically inducible Tet-system may be employed (Gatz, Mol. Gen. Genet. 227 (1991); 229-237). Further suitable promoters are known to the person skilled in the art and are described, e.g., in Ward (Plant Mol. Biol. 22 (1993), 361-366). The regulatory elements may further comprise transcriptional and/or translational enhancers functional in plants cells. Furthermore, the regulatory elements may include transcription termination signals, such as a poly-A signal, which lead to the addition of a poly A tail to the transcript which may improve its stability; for literature see also supra.

In the case that a nucleic acid molecule according to the invention is expressed in sense orientation it is in principle possible to modify the coding sequence in such a way that the protein is located in any desired compartment of the plant cell. These include the endoplasmatic reticulum, the vacuole, the mitochondria, the plastids, the apoplast, the cytoplasm etc. Methods how to carry out this modifications and signal sequences ensuring localization in a desired compartment are well known to the person skilled in the art.

Methods for the introduction of foreign DNA into plants are also well known in the art. These include, for example, the transformation of plant cells or tissues with T-DNA using *Agrobacterium tumefaciens* or *Agrobacterium rhizogenes*, the fusion of protoplasts, direct gene transfer (see, e.g., EP-A 164 575), injection, electroporation, biolistic methods like particle bombardment and other methods known in the art. The vectors used in the method of the invention may contain further functional elements, for example "left border"- and "right border"-sequences of the T-DNA of *Agrobacterium* which allow for stably integration into the plant genome. Furthermore, methods and vectors are known to the person skilled in the art which permit the generation of marker free transgenic plants, i.e. the selectable or scorable marker gene is lost at a certain stage of plant development or plant breeding. This can be achieved by, for example cotransformation (Lyznik, Plant Mol. Biol. 13 (1989), 151-161; Peng, Plant Mol. Biol. 27 (1995), 91-104) and/or by using systems which utilize enzymes capable of promoting homologous recombination in plants (see, e.g., WO97/08331; Bayley, Plant Mol. Biol. 18 (1992), 353-361); Lloyd, Mol. Gen. Genet. 242 (1994), 653-657; Maeser, Mol. Gen. Genet. 230 (1991), 170-176; Onouchi, Nucl. Acids Res. 19 (1991), 6373-6378). Methods for the preparation of appropriate vectors are described by, e.g., Sambrook (Molecular Cloning; A Laboratory Manual, 2nd Edition (1989), Cold Spring Harbor Laboratory Press, Cold Spring Harbor, N.Y.).

Suitable strains of *Agrobacterium tumefaciens* and vectors as well as transformation of *Agrobacteria* and appropriate growth and selection media are well known to those skilled in the art and are described in the prior art (GV3101 (pMK90RK), Koncz, Mol. Gen. Genet. 204 (1986), 383-396; C58C1 (pGV 3850kan), Deblaere, Nucl. Acid Res. 13 (1985), 4777; Bevan, Nucleic. Acid Res. 12(1984), 8711; Koncz, Proc. Natl. Acad. Sci. USA 86 (1989), 8467-8471; Koncz, Plant Mol. Biol. 20 (1992), 963-976; Koncz, Specialized vectors for gene tagging and expression studies. In: Plant Molecular Biology Manual Vol 2, Gelvin and Schilperoort (Eds.), Dordrecht, The Netherlands: Kluwer Academic Publ. (1994), 1-22; EP-A-120 516; Hoekema: The Binary Plant Vector System, Offsetdrukkerij Kanters B.V., Alblasserdam (1985), Chapter V, Fraley, Crit. Rev. Plant. Sci., 4, 1-46; An, EMBO J. 4 (1985), 277-287). Although the use of *Agrobacterium tumefaciens* is preferred in the method of the invention, other *Agrobacterium* strains, such as *Agrobacterium rhizogenes*, may be used, for example if a phenotype conferred by said strain is desired.

Methods for the transformation using biolistic methods are well known to the person skilled in the art; see, e.g., Wan, Plant Physiol. 104 (1994), 37-48; Vasil, Bio/Technology 11 (1;993), 1553-1558 and Christou (1996) Trends in Plant Science 1, 423-431. Microinjection can be performed as described in Potrykus and, Spangenberg (eds.), Gene Transfer To Plants. Springer Verlag, Berlin, N.Y. (1995).

The transformation of most dicotyledonous plants is possible with the methods described above. But also for the transformation of monocotyledonous plants several successful transformation techniques have been developed. These include the transformation using biolistic methods as, e.g., described above as well as protoplast transformation, electroporation of partially permeabilized cells, introduction of DNA using glass fibers, etc. The resulting transformed plant cell can then be used to regenerate a transformed plant in a manner known by a skilled person. This can be found, for example, in Hood, Molecular Breeding 3 (1997), 291-306; Coleman, Proc. Natl. Acad. Sci. USA 94 (1997), 7094-7097; Shilito, Biotechnology 7 (1989), 581-587.

In general, the plants which can be modified according to the invention and which either show overexpression of a protein according to the invention or a reduction of the synthesis of such a protein can be derived from any desired plant species. They can be monocotyledonous plants or dicotyledonous plants, preferably they belong to plant species of interest in agriculture, wood culture or horticulture interest, such as crop plants (e.g. maize, rice, barley, wheat, rye, oats etc.), potatoes, oil producing plants (e.g. oilseed rape, sunflower, pea nut, soy bean, etc.), cotton, sugar beet, sugar cane, leguminous plants (e.g. beans, peas etc.), wood producing plants, preferably trees, etc.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration. If desired, selectable genetic markers may be used consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

Thus a further aspect of the present invention provides a method of transforming a plant cell involving introduction of a vector comprising a nucleic acid of the present invention (e.g. R1 or R1 variant) into a plant cell and causing or allowing recombination between the vector and the plant cell genome to introduce the sequence of nucleotides into the genome.

The invention further encompasses a host cell transformed with nucleic acid molecule or a vector according to the present invention, especially a plant or a microbial cell. In the transgenic plant cell (i.e. transgenic for the nucleic acid in question) the transgene may be on an extra-genomic vector or incorporated, preferably stably, into the genome. There may be more than one heterologous nucleotide sequence per haploid genome.

The term "heterologous" is used broadly in this aspect to indicate that the gene/sequence of nucleotides in question have been introduced into said cells of the plant or an ancestor thereof, using genetic engineering, i.e. by human intervention. A heterologous gene may be additional to a corresponding endogenous gene. Nucleic acid heterologous, or exogenous or foreign, to a plant cell may be non-naturally occurring in cells of that type, variety or species. Thus the heterologous nucleic acid may comprise a coding sequence of or derived from a particular type of plant cell or species or variety of plant, placed within the context of a plant cell of a different type or species or variety of plant.

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., Cell Culture and Somatic Cell Genetics of Plants, Vol I, II and III, Laboratory Procedures and Their Applications, Academic Press, 1984, and Weissbach and Weissbach, Methods for Plant Molecular Biology, Academic Press, 1989.

The generation of fertile transgenic plants has been achieved in the cereals rice, maize, wheat, oat, and barley (reviewed in Shimamoto, K. (1994) Current Opinion in Biotechnology 5,158-162; Vasil, et al. (1992) Bio/Technology 10,667-674; Vain et al., 1995, Biotechnology Advances 13 (4): 653-671; Vasil, 1996, Nature Biotechnology 14 page 702).

Plants which include a plant cell according to the invention are also provided, along with any part or propagule thereof, seed, selfed or hybrid progeny and descendants. A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

In a preferred embodiment of the invention, the transgenic plant of the invention upon the presence of the R1 gene of the invention attained resistance or improved resistance against a pathogen the corresponding wild-type plant was susceptible to.

The term "resistance" covers the range of protection from a delay to complete inhibition of disease development. Examples for pathogens of importance comprise *Phytophthora infestans*, the causal agent of potato late blight disease, *Phytophthora sojae*, root rot pathogen of soybean, *Peronospora patasitica* (downy mildew); *Magnaporthe grisea*, causal agent of rice blast disease, *Erysiphe* spp (powdery mildew), *Pseudomonas syringae* (agent of bacterial blight), *Erwinia amylovora* (fire blight disease), *Erwinia carotovora* (soft rot), *Botrytis cinerea* (downy mildew of grape), *Rhizoctonia solani* and *Pythium debaryanum* (agents of seedling blight or damping off disease). Preferably, the transgenic plant of the invention attains resistance to *P. infestans*.

In addition to the regenerated plant, the present invention embraces all of the following: a clone of such a plant, seed, selfed or hybrid progeny and descendants (e.g. F1 and F2 descendants) and any part of any of these, such as cuttings, seed. The invention also provides a plant propagule from such a plant, that is any part which may be used in reproduction or propagation, sexual or asexual, including cuttings, seed and so on.

As an alternative to the molecular-biology based methods of introducing R1 (or variants thereof) into plants, the sequences disclosed herein may be used to facilitate selection of plants into which it is desired to introduce the resistance trait using conventional plant breeding methods. Progeny from crosses which carry the gene may be readily identified by screening on the basis of the R1 sequence, particularly the R1 signature sequence.

The methods disclosed herein for identifying proximal markers to the R1 locus may be generally applicable to other genes found in clusters (e.g. plant derived resistance genes). Such methods are characterised in that they employ a step using low stringency PCR with non-degenerate primers which avoid conserved sequence motifs. The general approach may be summarised as follows: (a) Prepare a population in which the gene of interest is segregating, (b) Identify resistance gene homologue (s) linked to the locus of interest on the basis of highly conserved (resistance gene) motifs and highly degenerate primers (Leister et al., 1996) Nature Genet. 14,421-428, (c) Identify further markers corresponding to homologous genes, which are within the (resistance) locus and that are closer to the gene, using low stringency PCR with nondegenerate primers which avoid conserved sequence motifs, (d) Use said further markers to identify a clone carrying the (resistance) gene of interest genomic library from a resistant plant, optionally in conjunction with transient assays for activity (Mindrinos et al (1994) or as described herein), (e) Optionally, confirm the identity of the cloned gene on the basis of phenotype in transgenic plants.

The present invention also encompasses the expression product of any of the R1 or variant nucleic acid sequences disclosed above, and methods of making the expression product by expression from encoding nucleic acid molecules therefore under suitable conditions, Which may be in suitable host cells in vitro, or chemically synthesized, in particular if antigens for raising antibodies are desired.

Antibodies may be raised to a purified R1/variant polypeptide or peptide by any method known in the art (for an overview see e.g. "Immunology-5th Edition" by Roitt, Brostoff, Male: Pub 1998-Mosby Press, London). Such antibodies, or fragments or derivatives thereof, can be used to bind R1 or in the identification and/or isolation of proteins homologous to R1 (i.e. which share epitopes therewith), which in turn can provide the basis of an alternative method to those described above to isolate their encoding genes.

Likewise, aptamers that bind to the R1 polypeptide of the invention may be employed. The preparation of aptamers is known to the person skilled in the art; see, e.g., Thomas, and Dinshaw (2000) Adaptive recognition by nucleic aptamers. Science 287:820-825.

The invention further provides a method of influencing or affecting a resistance trait in a plant, whereby the method includes the step of causing or allowing expression of a heterologous nucleic acid sequence as discussed above (e.g. R1 or R1 variant, in each case plus an optional elicitor) within cells of the plant.

As an alternative, it may be desirable to down-regulate R1 activity. This may be achieved, for instance used antisense technology (which is reviewed in Bourque, (1995), Plant Science 105,125-149, and Flavell, (1994) PNAS USA 91, 3490-3496). An alternative to anti-sense is to use a copy of all or part of the target gene inserted in sense, that is the same orientation as the target gene, to achieve reduction in expression of the target gene by cosuppression; see, for example, van der Krol et al., (1990) The Plant Cell 2, 291-299; Napoli et al., (1990) The Plant Cell 2, 279-289; Zhang et al., (1992) The Plant Cell 4, 1575-1588, and U.S. Pat. No. 5,231,020.

Thus, in the invention also relates to a transgenic plant cell—and to transgenic plants comprising such plants cells—which contain, preferably stably integrated into the genome, a nucleic acid molecule according to the invention or part thereof, wherein the transcription and/or expression of the nucleic acid molecule or part thereof leads to reduction of the synthesis of an R1 protein. In a preferred embodiment, the reduction is achieved by an anti-sense, sense, ribozyme, co-suppression, dominant mutant effect, or knock out mutant in the R1 gene.

Preferably, though, the invention provides a method which includes expressing SEQ ID NO:1 or a variant thereof within the cells of a plant (thereby producing the encoded polypeptide), following an earlier step of introduction of the nucleic acid into a cell of the plant or an ancestor thereof. Generally such a method may be used to introduce fungal resistance into the plant whereby an R1-mediated resistance is triggered by contact with an appropriate fungal elicitor or other initiator or inducer. Broadly speaking the elicitor or other trigger may be encoded directly by the invading fungi (such as the virulence protein of *P. infestans* or certain other fungi). Alternatively it may be expressed by a separate construct or transgene which is itself triggered or upregulated by the fungal infection. Additionally, in both of these cases, modification of the R1 (variant) sequence may allow triggering by a non-natural elicitor, if this is preferred.

The formats described above, to assess R1 or R1-derivative function with respect to a putative or known elicitor, themselves form a further aspect of the present invention. In particular the methods, for establishing gene for gene compatibility between elicitor and resistance gene, are characterised in that they include the steps of: (a) causing or permitting the co-expression in cell of R1 or an R1 derivative with the elicitor, (b) observing said cell for an HR, (c) correlating the result of the observation made in (b) with the specificity of the R1 or the R1 derivative for the elicitor.

In accordance with the above, the present invention also relates to such transgenic plants which are more sensitive to Late Blight infection compared to a corresponding wild type plant. Likewise, the present invention relates to harvestable parts and propagation material of such plants.

As described in the examples, an R1 gene has been isolated which upon transformation into a susceptible potato cultivar Desireé conferred resistance to *P. infestans*. Since the genomic clone the corresponding DNA sequence of which is depicted in SEQ ID NO:1 was able to give rise to this effect, it is apparent that the regulatory sequences of the R1 gene necessary and sufficient to mediate the expression of the R1 polypeptide upon pathogen infection are contained in the isolated DNA sequence. It is immediately evident to the person skilled in the art that such regulatory sequences have important applications on their own, for example for the expression of heterologous DNA sequences specifically upon pathogen infection, e.g., for the induction of a hypersensitive response to a given pathogen.

Accordingly, the present invention also relates to a regulatory sequence of a promoter naturally regulating the expression of a nucleic acid molecule of the invention described above or of a nucleic acid molecule homologous to a nucleic acid molecule of the invention, said regulatory sequence being capable of conferring or modulating the expression of a heterologous DNA sequence upon pathogen infection.

In context with the present invention, the term "regulatory sequence" refers to sequences which influence the specificity and/or level of expression, for example in the sense that they confer cell and/or tissue specificity. Such regions can be located upstream of the transcription initiation site, but can also be located downstream of it, e.g., in transcribed but not translated leader sequences, or in introns.

The term "promoter", within the meaning of the present invention refers to nucleotide sequences necessary, for transcription initiation, i.e. RNA polymerase binding and successful start of processive transcript formation, and may also include, for example, the TATA box.

The term "nucleic acid molecule homologous to a nucleic acid molecule of the invention", as used herein includes promoter regions and regulatory sequences of other R1 genes, such as genes from other species, for example, tomato which are homologous to potato R1 genes and which display substantially the same expression pattern. Such promoters are characterized by their capability of conferring preferably exclusively expression of a heterologous DNA sequence in a plant upon pathogen infection.

The term "capable of conferring or motulating the expression of a heterologous DNA sequence upon pathogen infection" as used herein means that said promoter is capable of controlling the expression of a heterologous DNA sequence in plants at infection sites, analogous or closely related to the controlled expression of pathogen related genes which are involved in the natural resistance in most incompatible host/pathogen interactions, such as the hypersensitive cell death at infection sites of a part of a plant. Thus, the regulatory sequence of the invention is characterized by its capability of mediating localized transcriptional activation selectively in response to pathogen attack or in response to stimuli that mimic pathogen attack such as elicitors prepared from, e.g., pathogens such as fungi or bacteria or derivatives thereof. The transcriptional activation by the regulatory sequence of the invention may also occur in cells surrounding the actual infection site due to cell-cell interactions. The regulatory sequence of the invention and chimeric promoters comprising such sequences may advantageously not or only to a small extent be inducible upon other stimuli such as abiotic stress. Preferably, the induction from the chimeric promoter upon pathogen attack or elicitor treatment is at least about 10-fold higher, preferably 20-fold higher and particularly 30-fold higher than its activation, if any, by abiotic stress.

However, the expression specificity conferred by the regulatory sequences of the invention may not be limited to local gene expression due to pathogens, for example, they may be combined with further regulatory sequences that provide for tissue specific gene expression. The particular expression pattern may also depend on the plant/vector system employed. However, expression of heterologous DNA sequences driven by the regulatory sequences of the invention predominantly occurs upon pathogen infection or treatment with a corresponding elicitor unless certain elements of the invention were taken and designed by the person skilled in the art to control the expression of a heterologous DNA sequence certain cell types.

Thus, according to the present invention, regulatory sequences from other species can be used that are functionally homologous to the regulatory sequences of the promoter of the above defined R1 specific nucleic acid molecules, or promoters of genes that display an identical or similar pattern of expression. The particular expression pattern may also depend on the plant/vector system employed. However, expression of heterologous DNA sequences driven by the regulatory sequences of the invention predominantly occurs in any cell infected by a particular pathogen unless certain elements of the regulatory sequences of the invention, were taken and designed by the person skilled in the art to control the expression of a heterologous DNA sequence in a particular tissue or otherwise controlled manner.

In accordance with the present invention, novel regulatory sequences of R1 genes, can be isolated and have been exemplified for the regulatory sequence of the R1 gene of potato. For example, genomic DNA can be digested with appropriate restriction enzymes, denatured and allowed to anneal to a reverse primer derived from the cDNA sequence of the invention. After primer extension, a blunt-ended adaptor can be ligated and PCR can be performed using a nested reverse primer derived from the mentioned cDNA, and a forward primer derived from the adaptor sequence. In another strategy for the cloning of the regulatory sequences of the invention a physical map of the genomic sequences upstream the coding region can be constructed by mean of genomic southern analysis. With this information, genomic DNA can be digested with selected restriction enzymes, genomic fragments containing a piece of the upstream sequences and the coding sequence can be gel purified and self-ligated in a large volume to favour the formation of circular molecules, that can subsequently be amplified by PCR with forward and reverse primers, derived from the coding sequence of the gene. Within the cloned genomic sequence, the transcription start site can be determined by standard procedures well known to everyone skilled in the art, such as 5'-RACE, primer extension or S1 mapping. To define cis-regulatory elements upstream of the transcription start site (i.e. within the putative promoter region), the respective region is fused to marker genes such as genes encoding GUS or GFP, and 5' deletion derivatives of these construct are generated. They are transformed into suitable plant material, and the expression of the marker gene depending on the remaining upstream sequence (putative promoter) is determined. These techniques are well known to a person skilled in the art.

In one embodiment the regulatory sequence of the invention comprises a DNA sequence selected from the group consisting of (a) DNA sequences comprising the nucleotide sequence as depicted in SEQ ID NO. 1 from nucleotides 1 to 2222 or (a) part(s) thereof;

(b) DNA sequences comprising at least 14 consecutive nucleotides of the nucleotide sequence as depicted in SEQ ID NO: 1 from nucleotides 1 to 2222;

(c) DNA sequences hybridizing with a nucleotide sequence as defined in (a) or (b) under stringent conditions;

(d) DNA sequences of a gene of fragment thereof obtainable by screening an appropriate genomic DNA library with a probe having a nucleotide sequence as defined in claim 1; and (e) DNA sequences comprising nucleotide sequences which are conserved in (a), (b) and (c).

Homologous regulatory sequences differ at one or more positions from the regulatory sequence of (a) or (b) but still have the same specificity, namely they comprise the same or similar sequence motifs, preferably 6 to 10 nucleotides in length, responsible for the above described expression pattern. Preferably such regulatory sequences hybridize to one of the above-mentioned regulatory sequences, most preferably under stringent conditions. Particularly preferred are regulatory sequences which share at least 85%, more preferably 90-95%, and most preferably 96-99% sequence identity with one of the above-mentioned regulatory sequences and have the same or substantially the same specificity. Such regulatory sequences also comprise those which are altered, for example by one or more nucleotide deletion(s), insertion(s), substitution(s), addition(s), and/or recombination(s) and/or any other modification(s) known in the art either alone or in combination in comparison to the above-described nucleotide sequence. Methods for introducing such modifications in the nucleotide sequence of the regulatory sequences of the invention are well known to the person skilled in the art. It is also immediately evident to the person skilled in the art that further regulatory elements may be added to the regulatory sequences of the invention. For example, transcriptional enhancers and/or sequences which allow for induced expression of the regulatory sequences of the invention may be employed. A suitable inducible system is for example tetracycline-regulated gene expression as described, e.g., by Gatz, supra.

The possibility exists to modify the regulatory sequences as described above or sequence motifs thereof by, e.g., nucleotide replacements which do not affect the overall structure or binding motif of the regulatory sequence so that it remains capable of conferring gene expression upon pathogen infection. The regulatory sequence of the invention may be derived from the R1 genes of potato (see Examples) although other plants may be suitable sources for such regulatory sequences as well. Furthermore, the nucleotide sequences of the invention can be compared as appropriate computer programs known in the art such as BLAST, which stands for Basic Local Alignment Search Tool (Altschul, 1997; Altschul, J. Mol. Evol. 36 (1993), 290-390; Altschul, J. Mol. Biol. 215 (1990); 403-410), can be used to search for local sequence alignments. BLAST produces alignments of nucleotide sequences to determine sequence similarity. Because of the local nature of the alignments, BLAST is especially useful in determining exact matches or in identifying homologues. With such means it is possible to identify conserved nucleotide sequences that may play a role in pathogen specific expression.

Usually, said regulatory sequence is part of a recombinant DNA molecule. In a preferred embodiment of the present invention, the regulatory sequence in the recombinant DNA molecule is operatively linked to a heterologous DNA sequence. The term heterologous with respect to the DNA sequence being operatively linked to the regulatory sequence of the invention means that said DNA sequence is not naturally linked to the regulatory sequence of the invention. Expression of said heterologous DNA sequence comprises transcription of the DNA sequence, preferably into a translatable mRNA. Regulatory elements ensuring expression in eukaryotic cells, preferably plant cells, are well known to those skilled in the art. They usually comprise poly-A signals ensuring termination of transcription and stabilization of the transcript, see also supra. Additional regulatory elements may include transcriptional as well as translational enhancers; see supra.

In a preferred embodiment, the heterologous DNA sequence of the above-described recombinant DNA molecules encodes a peptide, protein, antisense RNA, sense RNA and/or ribozyme. The recombinant DNA molecule of the invention can be used alone or as part of a vector to express heterologous DNA sequences, which, e.g., encode proteins for, e.g., seed storage proteins, toxins, antibodies ("plantibodies") or diagnostics of R1 related gene expression. The recombinant DNA molecule or vector containing the DNA sequence encoding a protein of interest is introduced into the cells which in turn produce the protein of interest. For example, the regulatory sequences of the invention can be operatively linked to sequences encoding Barstar and Barnase, respectively, for use in the production of HR response in plants. Applications of the regulatory sequences of the invention are evident to the person skilled in the art and can be derived from the literature, e.g., Strittmatter and Wegener, Zeitschrift für Naturforschung 48c (1993), 673-688; Kahl, J. Microbiol. Biotechnol. 11 (1995), 449-460 and references cited therein.

On the other hand, said protein can be a scorable marker, e.g., luciferase, green fluorescent protein or β-galactosidase. This embodiment is particularly useful for simple and rapid screening methods for compounds and substances described herein below capable of modulating R1 gene expression. For example, a transgenic plant can be cultured in the presence and absence of a candidate compound in order to determine whether the compound affects the expression of genes which are under the control of regulatory sequences of the invention, which can be measured, e.g., by monitoring the expression of the above-mentioned marker. It is also immediately evident to those skilled in the art that other marker genes may be employed as well, encoding, for example, a selectable marker which provides for the direct selection of compounds which induce or inhibit the expression of said marker.

The regulatory sequences of the invention may also be used in methods of antisense approaches. The antisense RNA may be a short (generally at least 10, preferably at least 14 nucleotides, and optionally up to 100 or more nucleotides) nucleotide sequence formulated to be complementary to a portion of a specific mRNA sequence and/or DNA sequence of the gene of interest. Standard methods relating to antisense technology have been described; see, e.g., Klann, Plant Physiol. 112 (1996), 1321-1330 and supra. Following transcription of the DNA sequence into antisense RNA, the antisense RNA binds to its target sequence within a cell, thereby inhibiting translation of the mRNA and down-regulating expression of the protein encoded by the mRNA.

In a further embodiment, the invention relates to nucleic acid molecules of at least 15 nucleotides in length hybridizing specifically with a regulatory sequence as described above or with a complementary strand thereof. Specific hybridization occurs preferably under stringent conditions and implies no or very little cross-hybridization with nucleotide sequences having no or substantially different regulatory properties. Such nucleic acid molecules may be used as probes and/or for the control of gene expression. Nucleic acid probe technology is well known to those skilled in the art who will readily appreciate that such probes may vary in length. Preferred are nucleic acid probes of 17 to 35 nucleotides in length. Of course, it may also be appropriate to use nucleic acids of up to 100 and more nucleotides in length. The nucleic acid probes of the invention are useful for various applications. On the one hand, they may be used as PCR primers for amplification of regulatory sequences according to the invention. Another application is the use as a hybridization probe, to identify regulatory sequences hybridizing to the regulatory sequences of the invention by homology screening of genomic DNA libraries. Nucleic acid molecules according to this preferred embodiment of the invention which are complementary to a regulatory sequence as described above may also be used for repression of expression of a gene comprising such regulatory sequences, for example due to an antisense, cosuppression or triple helix effect or for the construction of appropriate ribozymes (see, e.g., EP-B1 0 291 533, EP-A1 0 321 201, EP-A2 0 360 257) which specifically cleave the (pre)-mRNA of a gene comprising a regulatory sequence of the invention. Selection of appropriate target sites and corresponding ribozymes can be done as described for example in Steinecke, Ribozymes, Methods in Cell Biology 50, Galbraith et al. eds Academic Press, Inc. (1995), 44.9-460. Furthermore, the person skilled in the art is well aware that it is also possible to label such a nucleic acid probe with an appropriate marker for specific applications, such as for the detection of the presence of a nucleic acid molecule of the invention in a sample derived from an organism.

The above described nucleic acid molecules may either be DNA or RNA or a hybrid thereof. Furthermore, said nucleic acid molecule may contain, for example, thioester bonds and/or nucleotide analogues, commonly used in oligonucleotide anti-sense approaches; see supra.

The present invention also relates to vectors, particularly plasmids, cosmids, viruses and bacteriophages used conventionally in genetic engineering that comprise a regulatory sequence or corresponding recombinant DNA molecule of the invention.

Preferably, said vector is an expression vector and/or a vector further comprising a selection marker for plants. For example of suitable selector markers, see supra. Methods which are well known to those skilled in the art can be used to construct recombinant vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the recombinant DNA molecules and vectors of the invention can be reconstituted into liposomes for delivery to target cells.

The present invention furthermore relates to host cells transformed with a regulatory sequence, a DNA molecule or vector of the invention. Said host cell may be a prokaryotic or eukaryotic cell. The regulatory sequence, vector or recombinant DNA molecule of the invention which is present in the host cell may either be integrated into the genome of the host cell or it may be maintained extrachromosomally. The host cell can be any prokaryotic or eukaryotic cell, such as a bacterial, insect, fungal, plant, animal or human cell. Preferred cells are plant cells.

In a further preferred embodiment, the present invention provides for a method for the production of transgenic plants, plant cells or plant tissue comprising the introduction of a nucleic acid molecule, recombinant DNA molecule or vector of the invention into the genome of said plant, plant cell or plant tissue. For the expression of the heterologous DNA sequence under the control of the regulatory sequence according to the invention in plant cells, further regulatory sequences such as poly A tail may be fused, preferably 3' to the heterologous DNA sequence, see also supra. Further possibilities might be to add transcriptional or translational enhancers that increase gene expression, or sequences that increase mRNA stability. Methods for the introduction of foreign DNA into plants, plant cells and plant tissue are described above.

Thus, the present invention relates also to transgenic plant cells which contain, preferably stably integrated into the genome, a regulatory sequence, a recombinant DNA molecule or vector according to the invention. Furthermore, the present invention also relates to transgenic plants and plant tissue comprising the above-described transgenic plant cells.

Furthermore, the present invention relates to a method for the identification of a plant protective agent comprising the steps of:

(a) culturing a plant cell or tissue or maintaining a plant comprising a recombinant DNA molecule comprising a readout system operatively linked to a regulatory sequence of the present invention in the presence of a compound or a sample comprising a plurality of compounds under conditions which permit expression of said readout system;

(b) identifying or verifying a sample and compound, respectively, which leads to suppression or activation and/or enhancement of expression of said readout system in said plant, plant cell, or plant tissue.

The term "read out system" in context with the present invention means a DNA sequence which upon transcription and/or expression in a cell, tissue or organism provides for a scorable and/or selectable phenotype. Such read out systems are well known to those skilled in the art and comprise, for example, recombinant DNA molecules and marker genes as described above.

The term "plurality of compounds" in a method of the invention is to be understood as a plurality of substances which may or may not be identical.

Said compound or plurality of compounds may be inorganic or organic, naturally occurring or man made compounds and may be comprised in, for example, samples, e.g., cell extracts from, e.g., plants, animals or microorganisms. Furthermore, said compound(s) may be known in the art but hitherto not known to be capable of suppressing or activating and/or enhancing the transcription of an R1 gene. The plurality of compounds may be, e.g., added to the culture medium or injected into the plant, plant cells or tissue or sprayed onto the plant or supplied in the soil.

If a sample containing a compound or a plurality of compounds is identified in the method of the invention, then it is either possible to isolate the compound from the original sample identified as containing the compound capable of suppressing or activating and/or enhancing the transcription of a R1 gene, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. Preferably, the compound identified according to the above described method is further formulated in a form suitable for the application in plant breeding or plant cell and tissue culture.

The compounds which can be tested and identified according to a method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879-880; Hupp, Cell 83 (1995), 237-245; Gibbs, Cell 79 (1994), 193-198 and references cited supra). Furthermore, genes encoding a putative regulator of an R1 gene may be identified using, for example, insertion mutagenesis using, for example, gene targeting vectors known in the art (see, e.g., Hayashi, Science 258 (1992), 1350-1353; Fritze and Walden, Gene activation by T-DNA tagging. In *Methods in Molecular biology* 44 (Gartland, K. M. A. and Davey, M. R., eds). Totowa: Human Press (1995), 281-294) or transposon tagging (Chandlee, Physiologia Plantarum 78 (1990), 105-115). Said compounds can also be functional derivatives or analogues of known inhibitors or activators. Methods for the preparation of chemical derivatives and analogues; are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, N.Y., USA. Furthermore, said derivatives and analogues can, be tested for their effects according to methods known in the art. Furthermore, peptidomimetics and/or computer aided design of appropriate derivatives and analogues can be used, for example, according to the methods described above.

Determining whether a compound is capable of suppressing or activating and/or enhancing the transcription of an R1 gene can be done, for example, in plants by monitoring the reporter gene. It can further be done by monitoring the phenotypic characteristics of the transgenic plant of the invention contacted with the compounds and compare it to that of wild-type plants. In an additional embodiment, said characteristics may be compared to that of a transgenic plant contacted with a compound which is either known to be capable or incapable of suppressing or activating and/or enhancing R1 gene expression or the activity of the protein. The compounds identified according to the method of the invention are expected to be very beneficial since promoters that have been known so far are only of limited use due to the non or not tightly regulated pathogen specificity of their regulatory sequences.

The inhibitor or activator identified by the above-described method may prove useful as a herbicide, pesticide and/or as a plant growth regulator. Thus, in a further embodiment the invention relates to a compound obtained or identified according to the method of the invention. Such useful compounds can be for example transacting factors which bind to the regulatory sequence of the invention. Identification of transacting factors can be carried out using standard methods in the art (see, e.g., Sambrook, supra, and Ausubel, supra). To determine whether a protein binds to the regulatory sequences of the invention, standard DNA footprinting and/or native gel-shift analyses can be carried out. In order to identify a transacting factor which binds to the regulatory sequence of the invention, the regulatory sequence can be used as an affinity reagent in standard protein purification methods, or as a probe for screening an expression library. Once the transacting factor is identified, modulation of its binding to the regulatory sequences of the invention can be pursued, beginning with, for example, screening for inhibitors against the binding of the transacting factor to the regulatory sequences of the present invention. Activation or repression of R1 genes could then be achieved in plants by applying of the transacting factor (or its inhibitor) or the gene encoding it, e.g. in a vector for transgenic plants. In addition, if the active form of the transacting factor is a dimer, dominant-negative mutants of the transacting factor could be made in order to inhibit its activity. Furthermore, upon identification of the transacting factor, further components in the pathway leading to activation (e.g. signal transduction) or repression of a gene under the control of the regulatory sequences of the present invention can then be identified. Modulation of the activities of these components can then be pursued, in order to develop additional drugs and methods for modulating the expression of a gene under the control of the regulatory sequences of the present invention.

Preferably, the compound identified according to the above described method or its analog or derivative is further formulated in a form suitable for the application in plant breeding or plant cell and tissue culture. For example, it can be combined with a agriculturally acceptable carrier known in the art. The plant protection composition can be prepared by employing the above-described method of the invention and synthesizing the compound identified as inhibitor or activator in an amount sufficient for use in agriculture. Thus, the present invention also relates to a method for the preparation of an agricultural plant protection composition comprising the above-described steps of the method of the invention and synthesizing the compound so identified or an analog or derivative thereof.

In the plant protection composition of the invention, the compound identified by the above-described method may be preferentially formulated by conventional means commonly used for the application of, for example, herbicides and pesticides or agents capable of inducing systemic acquired resistance (SAR). For example, certain additives known to those skilled in the art comprising stabilizers or substances which facilitate the uptake by the plant cell, plant tissue or plant may be used, for example, carborundum, or 0.01% SDS (sodium dodecylsulfate) solution.

In a still further embodiment the present invention relates to a method for identifying and obtaining an avirulence or a virulence factor of a pathogen comprising the steps of:

(a) screening the R1 protein of the present invention or a fragment thereof against a peptide or protein expression library derived from a pathogen in a readout system under suitable conditions which permit interaction of the protein and peptide in said readout system;

(b) identifying or verifying a cDNA which leads to suppression or activation of the readout system.

Beside the above described possibilities of using the nucleic acid molecules according to the invention for the genetic engineering of plants with modified characteristics and their use to identify homologous molecules, the described nucleic acid molecules may also be used for several other applications, for example, for the identification of nucleic acid molecules which encode proteins which interact with the R1 proteins described above. This can be achieved by assays well known in the art, for example, as described in Scofield (Science 274 (1996), 2063-2065) by use of the so-called yeast "two-hybrid system". In this system the protein encoded by the nucleic acid molecules according to the invention or a smaller part thereof is linked to the DNA-binding domain of the GAL4 transcription factor. A yeast strain expressing this fusion protein and comprising a lacZ reporter gene driven by an appropriate promoter, which is recognized by the GAL4 transcription factor, is transformed with a library of cDNAs which will express plant proteins or peptides thereof fused to an activation domain. Thus, if a peptide encoded by one of the cDNAs is able to interact with the fusion peptide comprising a peptide of a protein of the invention, the complex is able to direct expression of the reporter gene. In this way the nucleic acid molecules according to the invention and the encoded peptide can be used to identify peptides and proteins interacting With R1 proteins. This method can also be employed for identifying inhibitors and activators as described above.

Other methods for identifying compounds which interact with the proteins according to the invention or nucleic acid molecules encoding such molecules are, for example, the in vitro screening with the phage display system as well as filter binding assays or "real time" measuring of interaction using, for example, the BIAcore apparatus (Pharmacia); see references cited supra.

A similar strategy can be pursued with the so called three hybrid system.

The yeast two-hybrid system originally has been described by Fields and Song (Nature 340 (1989), 245-246; see also for review Vidal, M, in Bartel, P. L. and Fields, S. (eds.), The yeast two-hybrid system. Oxford University Press, New York, N.Y., (1997), 109-147). A modified version of the yeast two-hybrid system has been described by (Gyuris, Cell 75 (1993), 223-232; Zervos, Cell 72 (1993); 223-232). Briefly, a domain of the polypeptide is used as bait for binding compounds. Positives are then selected by their ability to grow on plates lacking leucine, and then further tested for their ability to turn blue on plates with X-gal, as previously described in great detail; see also WO 95/31544. A modified version is the "reverse yeast two-hybrid system" which allows to select for interaction defective alleles using a negative selection strategy as, for example, described in (Vidal, Proc. Natl. Acad. Sci. USA 93 (1996), 10321-10326; Vidal, Proc. Natl Acad Sci. USA 93 (1996), 10315-10320). This system uses the counter selectable reporter gene URA3. Yeast cells expressing Ura3p convert the compound 5-flourootic acid (FOA) into the toxic derivative 5-flourouracil. A two-hybrid interaction which leads to activation of the URA3 reporter gene can, thus, be counterselected in the presence of FOA and loss of function mutants can be specifically selected out of a large pool of wild type alleles.

Another convenient method, for example, could be the yeast three-hybrid system as described (SenGupta, Proc. Natl. Acad. Sci. USA 93 (1996), 8496-8501). The yeast three-hybrid selection system was developed for isolating the genes of the proteins that interact with RNA, and to study RNA-protein interactions. This system, based on the yeast two-hybrid system, consists of a DNA-binding domain fused to a known RNA-binding protein, an activation domain fused to a prospective RNA-binding protein, and a hybrid RNA. Transcription of reporter genes only occurs when both hybrid proteins interact with the hybrid RNA. In the reverse three-hybrid system, interaction of the proteins with the hybrid RNA results in expression of a reporter gene whose product is toxic to yeast cells. All these methods can be employed in accordance with the above described method of the invention with the R1 protein or peptide fragments thereof as a bait for identifying and obtaining an avirulence or virulence factor and their encoding cDNAs or parts thereof. Methods for obtaining the DNA sequence of those clones tested positive in the screening assay are known to the person skilled in the art and are described in the above referenced publications.

The present invention also relates to the cDNA and its encoded product obtained or identified by the above described method.

The invention also relates to compositions comprising at least one of the aforementioned nucleic acid molecules and/or comprising a nucleic acid molecule which is complementary for such a nucleic acid molecule, a vector of the invention, a R1 protein of the invention or an immunologically or biologically active fragment thereof or an antibody cor aptamer specifically recognizing such a protein or fragment; a regulatory sequence or recombinant DNA, or a corresponding vector of the invention, a compound designed orientated according to the protein of the invention and/or identified according to the method described above and/or an antibody specifically recognizing such a compound or a regulatory sequence of the invention, and optionally suitable means for detection or mitable means for plant cell and tissue culture.

Diagnostic compositions may be used for methods for detecting expression of R1 gene by detecting the presence of corresponding mRNA which comprises isolation of mRNA from a cell and contacting the mRNA so obtained with a probe comprising a nucleic acid probe as described above under hybridizing conditions, detecting the presence of mRNA hybridized to the probe, and thereby detecting the expression of the gene by the cell. Further methods of detecting the presence of a protein according to the present invention comprises immunotechniques well known in the art, for example enzyme linked immunosorbent assay.

Moreover, the present invention relates to a kit comprising at least one of the aforementioned nucleic acid molecules, vectors, proteins, compounds, antibodies, or aptamers of the invention. The kit of the invention may contain further ingredients such as selection markers and components for selective media suitable for the generation of transgenic plant cells, plant tissue or plants. Furthermore, the kit may include buffers and substrates for reporter genes that may be present in the recombinant gene or vector of the invention. The kit of the invention may advantageously be used for carrying out the method of the invention and could be, inter alia, employed in a variety of applications referred to herein, e.g., in the diagnostic field or as research tool. The parts of the kit of the invention can be packaged individually in vials or in combination in containers or multicontainer units. Manufacture of the kit follows preferably standard procedures which are known to the person skilled in the art. The kit or its ingredients according to the invention can be, used in plant cell and plant tissue cultures, for example, for any of the above described methods or detecting inhibitors and activators of R1 genes. The kit of the invention and its ingredients are expected to be very useful in breeding new varieties of, for example, plants which display improved properties such as nutritial value or disease resistance.

It is also immediately evident to the person skilled in the art that the regulatory sequences, recombinant DNA molecules, vectors and compounds of the present invention can be employed to produce transgenic plants with a desired trait; see for review TIPTEC Plant Product & Crop Biotechnology 13 (1995), 312-397.

Furthermore, it is possible to use the nucleic acid molecules according to the (invention as molecular markers in plant breeding. Moreover, the overexpression of nucleic acid molecules according to the invention may be useful for the alteration or modification of plant/pathogen interaction. The term "pathogene" includes, for example, bacteria, viruses and fungi as well as protozoa. Preferably, said pathogene is *P. infestans*.

Furthermore, the present invention relates to the use of a nucleic acid molecule, vector, host cell, protein, a regulatory sequence, an aptamer recombinant DNA molecule, a vector, a compound an aptamer and/or the antibody of the invention for use in a screening method for the identification of virulence and avirulence genes of pathogens, for screening plant protective compounds, for inducing pathogen resistance in plants, as a marker in marker-assisted plant breeding. The regulatory sequence or a recombinant DNA molecule of the present invention is preferably used for the expression of a heterologous DNA sequence.

These and other embodiments are disclosed and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet. An overview of patent information in biotechnology and a survey of relevant sources of patent information useful for retrospective searching and for current awareness is given in Berks, TIBTECH 12 (1994), 352- 364.

The present invention is further described by reference to the following non-limiting figures and examples.

DETAILED DESCRIPTION OF THE INVENTION

EXAMPLES

Material and Methods

Figure 1:
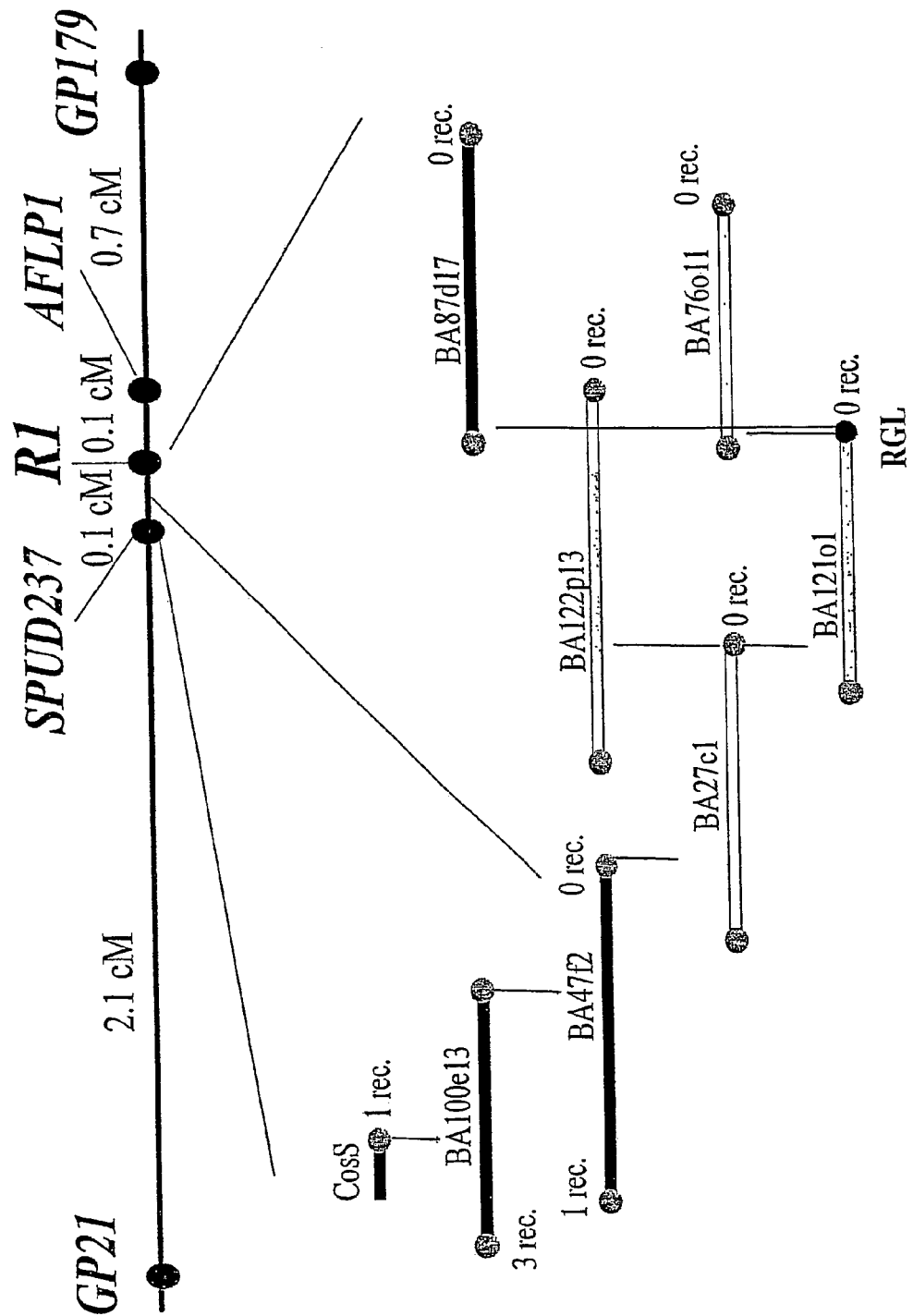
FIG. 1. Genetic and physical map of the R1 region. GP21 and GP179 are the markers used to construct the high-resolution map of the R1 region. SPUD237 and AFLP1 are converted AFLP markers (Meksem et al. 1995, De Jong et al. 1997) flanking R1. Genetic distances are given in cM. CosS is a cosmid clone selected with SPUD237. Remaining clones in the physical map are BACs with lengths between 70 and 90 kb. Solid black bars: BACs from the chromosome carrying R1. Grey bars: BACs from the chromosome carrying r1. White bar: BAC origin not determined. Mapped BAC ends are indicated by the number of recombinants separating the BAC end from R1. Cosmid and BAC ends used for chromosome walking are indicated by the vertical arrows. RGL: resistance-gene-like fragment.

Plant Material:

F1 offspring of a cross between the heterozygous diploid clones H79.1506/1 (R1 r1) and H80.696/4 (r1 r1), referred to as P41 and P40, respectively (Gebhardt et al. 1989, Leonards-Schippers et al. 1992), was used for high-resolution genetic mapping of R1. Recombinants in the marker interval GP21-

GP179 originating from the P41 (R1r1) parent were selected as described (Meksem et al. 1995). The hybrid clone P6/210 derived from the cross P41×P40 (Leister et al. 1997) which carries R1 in the heterozygous state was used for constructing genomic cosmid and BAC libraries. Parent P41 (R1r1) was used for cDNA library construction.

Test for Resistance to *Phytophthora infestans*:

Resistance to a *P. infestans* isolate having the corresponding avirulence factor Avr1 (race 4) was determined as described (Leonards-Schippers et al. 1992), except that whole leaflets instead of leaf disks were used for inoculation. Presence our absence of hypersensitive response (HR) was scored 8-10 days post inoculation.

Potato Genomic Libraries:

The BAC library was supplied by LION Bioscience AG (Heidelberg, Germany). The library has been constructed from HindIII partially digested high molecular weight genomic DNA of clone P6/210 in the binary vector pCLD04541 (Jones et al. 1992) as described (Meksem et al. 2000). The BAC library consists of 101.376 clones with an insert average size of 70 kb. The colonies were stored in 264 384-microtiter plates (Genetix, Oxford, UK) in 2YT medium (Sambrook et al. 1989) with freezing buffer (5.5% w/v glycin, 7 mM $(NH_4)SO_4$, 1.5 mM Na-Citrate, 0.3 mM $MgSO_4$, 13 mM $KH_2PO_4$, 27 mM $K_2HPO_4$).

A cosmid library of ca. 150 000 clones was constructed using standard procedures (Sambrook et al. 1989) from Sau3AI partially digested genomic DNA (17-23 kb fragments) of P6/210 and in the same vector (BamH1 cloning site) as the BAC library. Cosmids were packaged using Gigapack II Gold Packaging extract (Stratagene, Calif., USA) and transfected into *E. coli* strain SURE™ (Stratagene, Calif., USA). Plasmid DNA was extracted from pools of about 1500 bacterial colonies (Sambrook et al. 1989). One hundred and three cosmid pools were generated and screened by PCR using SPUD237 specific primers (De Jong et al. 1997). Positive pools were plated and screened by colony hybridisation using standard protocols (Sambrook et al. 1989).

BAC Library Screening and Contig Construction:

High-density colony filters for hybridisation-based screening of the BAC library were prepared using a BioGRID robot (Oxford, UK). Clones were gridded in double spots using a 5×5 array with 6×384 arrays per 22.5×22.5 cm nylon membrane (PALL, Biodyne, Portsmouth, UK). Each 5×5 array contained 2×12 colonies with the control position of the array occupied by the clone pSW1 (PE Biosystems, Foster City, Calif. USA). This gridding pattern allowed 27,648 colonies to be represented twice on each filter. Library screening was performed using a set of four filters carrying 101,376 clones. Colony filters were incubated on LB medium for 15 h at 37° C. and processed for colony hybridisation using standard techniques (Sambrook et al. 1989). Filter hybridisation was performed as described (Gebhardt et al. 1989), except that 300 pg pSW1 control insert were labelled and hybridised together with the probe to facilitate the determination of addresses of positive clones. Plasmid DNA was purified from positive clones and insertions were sequenced from both ends employing T3 and T7 oligonucleotides as sequencing primers. DNA sequence information of BAC insertion ends Was used to design specific PCR primer pairs. PCR products amplified with these primers and the respective BACs as template were used as probes for new filter hybridisation to identify overlapping BAC clones, for orientation of overlapping BAC clones relative to each other and for mapping in the recombinant plants. Overlaps were confirmed by sequencing the PCR products. Direction of contig extension was verified by genetic mapping using the recombinant plants and RFLP or PCR based marker analysis. To determine the size of BAC insertions, the BAC DNA was digested with NotI and the fragments were separated by pulsed field gel electrophoresis on a CHEF DRIII (BioRad, Hercules, Calif., USA) for 12 h at 1° C. with an initial pulse time of 5 s and a final pulse time of 1.0 s, at 120° angle and 6 V/cm.

BAC DNA Isolation:

BAC DNA was extracted using QIAfilter Plasmid Purification Kit 100 (Qiagen, Hilden, Germany) according to manufactures instructions with minor modifications. A single colony was precultured in liquid LB medium for 8 h at 37° C. 75 µl preculture were added to 75 ml LB medium and further incubated for 15 h at 37° C. A centrifugation step was introduced before passing the supernatant through the QIAfilter to remove bacterial cellular debris.

Preparation of Probes from BAC Insertions:

1.5 µg BAC DNA were digested to completion with HindIII plus EcoR1 and separated from the vector on 0.8% low melting temperature agarose (Sea Plaque GTG Agarose, Bioproducts, Rockland, Me., USA). Inserted DNA was dissolved from the gel using the GELase system; (Epicentre Technologies or Biozym) following the supplier's instructions. The DNA was ethanol precipitated, dissolved in water and labelled with $^{32}P$-dCTP by random primed labelling (Feinberg and Vogelstein 1984).

Subcloning of BAC BA87d17:

10 µg BAC DNA were partially digested with 1 U Tsp509I for 15 min at 65° C. and size separated on a 0.8% low melting temperature agarose gel (Sea Plaque GTG Agarose, Bioproducts, Rockland, Me., USA). Fragments of about 10 kb in size were eluted using the GELase system (Epicentre Technologies, Madison, USA), following the supplier's instructions. The purified fragments were cloned into the pCLD04541: binary vector linearized with EcoRI, dephosphorylated using SHRIMP phosphatase (Roche, Germany) and transformed into *E. coli* strain DH10B (Life Technologies, USA). Two hundred recombinant colonies were picked into microtiter plates.

cDNA Library Construction and Screening:

Cut shoots of ca. 8 weeks old plants of parent P41 (R1r1) and of the susceptible cv Desirée were infected with *P. infestans* race 4 and maintained under a glass cylinder (to increase humidity) in water in a growth chamber at 17° C. with 16 h light. Under these conditions leaves of the susceptible control were overgrown by *P. infestans* mycelium after 8 days. Equal amounts of uninfected leaves of parent P41 and infected leaves 2h, 19h, 3d, 7d and 9d after inoculation were collected. Poly $A^+$ RNA was isolated using the RNeasy Plant Mini Kit or the Oligotex mRNA Mini Kit (Qiagen, Hilden, Germany) according to the supplier's instructions. A Lambda ZAP II cDNA library (Stratagene, Calif., USA) was constructed from the poly-$A^+$ RNA, following the manufacturer's instructions. The different cDNA preparations were pooled prior to ligation into the Lambda ZAP vector. $5 \times 10^5$ pfu's were plated and screened by plaque hybridisation (Sambrook et al. 1989) using as probe the insertions of BACs BA121o1 and BA76o11.

5'Rapid Amplification of cDNA Ends (RACE) Analysis:

Total RNA was isolated from uninfected leaf tissue of P41 (R1r1) using the RNeasy Plant Mini Kit (Qiagen, Hilden, Germany) according to supplier's instructions. RACE analysis was performed with 1 µg total RNA using the SMART™

Race cDNA Amplification Kit (Clontech, CA, USA) following the manufacturer's instructions. The nested gene-specific primers used for the PCR amplification were first RT1-1: 5'-AAACCCGGTGTTCCAAATCTAACACT-3' (SEQ ID NO: 3) and second RT2-1: 5'-CATGTAGTGAGGATATGT-CACGAGTG-3'. (SEQ ID NO: 4) The final PCR products of the RACE reaction were cloned into pGEM-T vector (Promega, CA, USA). Two independent clones were sequenced.

DNA Sequence Analysis:

Custom DNA sequencing was done by the ADIS unit at the Max Planck Institute for Breeding Research. The dideoxy chain-termination sequencing, method was employed using an ABI PRISM Dye Terminator Cycle Sequencing Ready Reaction Kit and an ABI377 automated DNA Sequencer (PE Biosystems, Foster City, Calif. USA).

DNA sequence analysis was done using the Wisconsin Package Version 10.0, Genetics Computer Group (GCG), Madison, Wis., USA. Sequence databases were searched with BlastX and other algorithms available through the National Center for Biotechnology Information, Bethesda, Md., USA and the ExPASY www server (Appel et al. 1994).

Transformation of *Agrobacterium tumefaciens:*

Subclone g10 of BAC BA87d17 was electroporated into *A. tumefaciens* strain LBA4404 according to Wen-jun and Forde (1989). Three *Agrobacterium* strains, LBAg10-2, LBAg10-5 and LBAg10-23 were used for potato transformation.

*Agrobacterium tumefaciens* Mediated Potato Transformation and Analysis of Transgenic Plants:

The susceptible potato cultivar Desirée was used in all transformation experiments. *Agrobacterium tumefaciens* mediated transformation was performed as described by. Rocha-Sosa et al. (1989), except that the MS-medium contained 250 mg/l Claforan. Kanamycin resistant transgenic plants were tested by the polymerase chain reaction (PCR) for presence of the g10 insert using the insert specific primers 87e (5'-ATTACAATGGGTTGAACTCAG-3' (SEQ ID NO: 5)) and 87s (5'-ACCTCTTTCAATTGTTCTGGTG-3' (SEQ ID NO: 6)). PCR conditions were: Ta at 55° C. for 45 sec and polymerisation at 72° C. for 60 seconds. Transgenic plants were screened with the R1 specific primers 76-2sf2 (5'-CACTCGTGACATATCCTCACTA-3' (SEQ ID NO: 7)) and 76-2SR (5'-CAACCCTGGCATGCCACG-3' (SEQ ID NO: 8)) derived from cDNA c76-2. PCR conditions were: Ta at 55° C. for 45 sec and polymerisation at 72° C. for 90 sec. Tests for resistance to *P. infestans* race 4 were done using three leaflets per plant in each test.

Example 1

High-Resolution Genetic Mapping of the R1 Locus

To facilitate physical mapping of the R1 locus, 16 recombinants between the markers GP21 and GP179 flanking R1 (Leonards-Schippers et al. 1992) were selected from 588 plants and tested for resistance to a *P. infestans* having the corresponding avirulence factor Avr1. Together with 15 recombinants previously selected in the same interval (Meksem et al. 1995), 31 recombinants in total were available in the interval GP21-GP179 from 1049 plants, corresponding to 3.0% recombination frequency (3 cM). Recombination frequencies between GP21 and R1 and between R1 and GP179 were 2.2% and 0.8%, respectively (Table 1).

TABLE 1

Number of recombinant individuals in the intervals GP21-R1, GP179-R1 and GP21-GP179, selected among 1049 plants of a segregating F1 population.

|  | GP21-R1 | GP179-R1 | GP21-GP179 |
| --- | --- | --- | --- |
| Number of recombinants | 23 | 8 | 31 |
| Recombinants with genotype R1r1 | 12 | 4 | 16 |
| Recombinants with genotype r1r1 | 11 | 4 | 15 |
| Recombination frequency (%) | 2.2 | 0.8 | 3.0 |

The markers SPUD237 and AFLP1, both mapping in the interval GP21-GP179 (De Jong et al. 1997, Meksem et al. 1995) flank the R1 locus. Both markers were separated from R1 by one recombination event in 1049 plants (0.1 cM, FIG. 1).

Example 2

Chromosome Walking Towards the R1 Locus and Identification of an R1 Candidate Gene Marker SPUD237 was used as probe for screening the cosmid library. One positive clone CosS (FIG. 1) was identified. End sequencing of the CosS insert generated a new marker separated by one recombination event (0.1 cM) from the R1 locus. Screening the BAC library with this marker identified BAC clone BA100e13. Three recombination events separated the distal end of BA100e13 from R1. The BA100e13 end proximal to R1 identified BA47f2. The BA47f2 end distal to R1 overlapped with BA100e13 and was separated from R1 by one recombination event. The proximal end co-segregated with R1, like all subsequent BAC ends analysed (right part of FIG. 1). The BA47f2 end that co-segregated with R1 identified clone BA27c1. The BA27c1 end not overlapping with BA47f2 identified clones BA122p13 and BA121o1. The end of BA121o1 that did not overlap with BA27c1 showed highly significant sequence similarity (37% identity, 56% similarity of translated amino acid sequence) to the tomato Prf gene for resistance to *Pseudomonas syringae* (Salmeron et al. 1996). This resistance-gene-like (RGL) fragment was used as probe to rescreen the BAC library. The RGL probe identified, in addition to BA122p13, several new positive clones of which two, BA87d17 and BA76o11, were further analysed. They contained full length copies of the RGL gene which was envisaged as a possible R1 candidate. The non-overlapping ends of BA76o11 and BA87d17 co-segregated with R1.

BAC end markers instrumental for physical map construction were also used to assign BAC clones to the P6/210 (R1r1) chromosome carrying either an r1 or the R1 allele. Clones BA100e13, BA47f2 and BA87d17 (FIG. 1) were in cis with the R1 allele, whereas clones BA121o1, BA122p13 and BA76o11 were derived from the homologue having r1 (FIG. 1). Clone BA27c1 could not be assigned to an r1 or R1 chromosome, based on the markers used.

Example 3

R1 Candidate cDNA Clones

Figure 4:
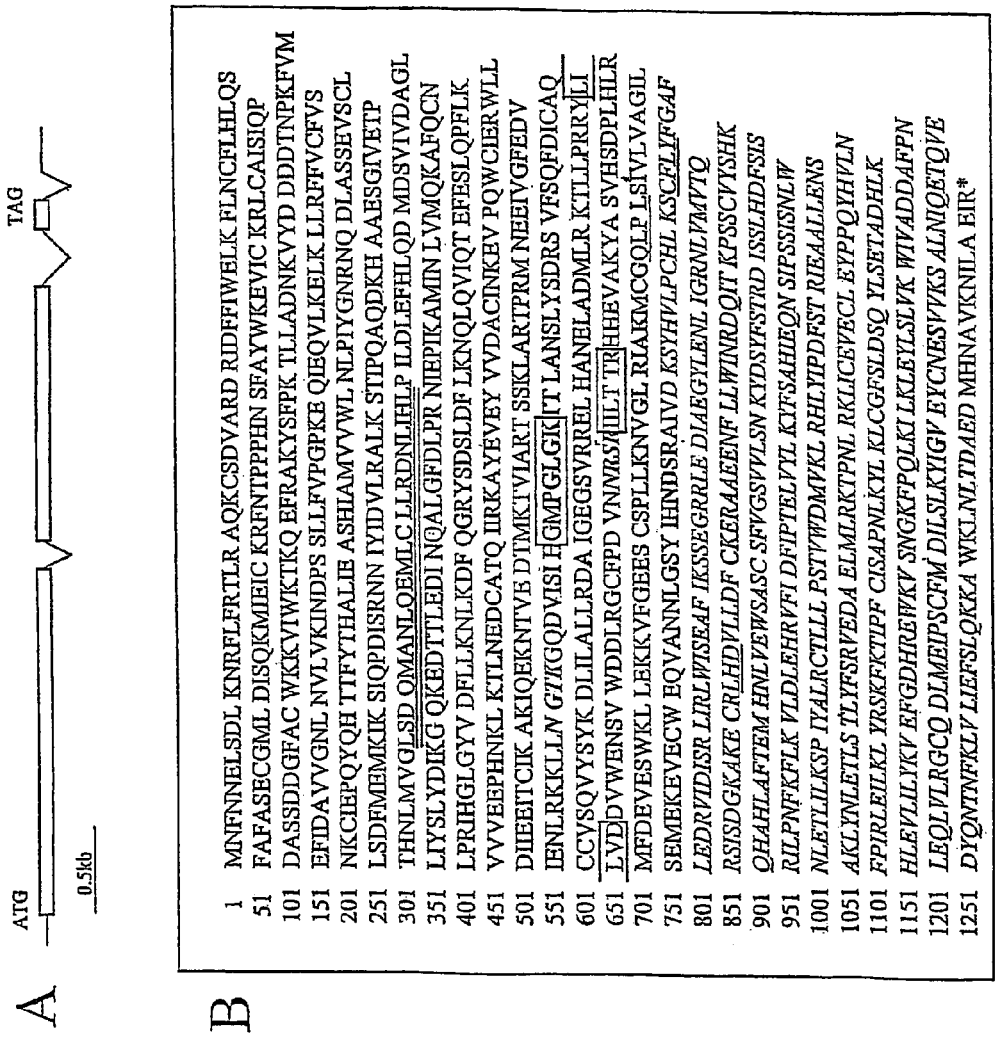
FIG. 4. The R1 gene. (A) Structural organisation. Exons are shown as boxes and introns as angeled lines. (B) The deduced amino acid sequence (SEQ ID NO: 2) The leucine-zipper motif is underlined twice. The LRR region is indicated in italics. The predicted kinase motifs are indicated inside the boxed region and N-glycosilation sites are indicated in bold. The conserved motifs QLPL, CFLY and LHD specific for plant resistance proteins, are underlined. Single letter codes for the amino acids are standard.

Using the whole insertions of BACs BA121o1 and BA76o11 as probes, six and eight cDNA clones, respectively, were isolated from a cDNA library prepared from infected leaves of genotype P41 (R1r1). Eight of the 14 cDNA clones were similar to known plant resistance genes. The highest similarity was obtained with the tomato Prf gene for resistance to *Pseudomonas syringae* (Salmeron et al. 1996). The sequences of the eight candidate cDNAs shared ca. 80-90, % identity among each other. The cDNA clone c76-2, 2292 nucleotides long, was identical, with exception of the introns, to the genomic sequence of clone g10, a subclone representing part of BA87d17 (see later). Sequence comparison to known resistance genes in the database indicated that c76-2 was not full length. Using RACE analysis, the cDNA was extended to the 0.5° end by 1943 nucleotides, resulting in a full-length cDNA sequence of 4235 nucleotides including a 5' untranslated region of 59 nucleotides and 297 nucleotides 3' untranslated sequence between the stop codon and the poly A tail. The cDNA included a start codon at position 2223 of the genomic sequence corresponding to the first methionine in the amino acid sequence deduced from clone g10 (FIG. 4B). Two adenines were identified at positions −3 and +4 (where the a of the ATG is +1) referred to as ribosome recognition sequence in plants, insects, yeast and mammals (Kozak 1991).

Figure 2:
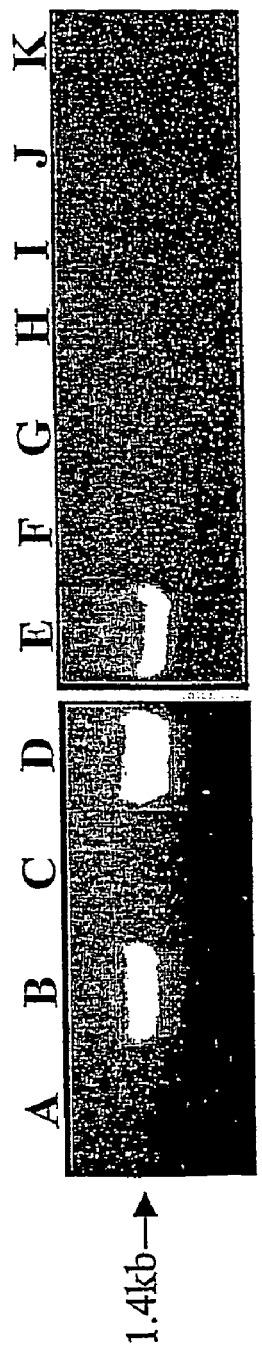
FIG. 2. PCR amplification of a 1.4 kb fragment of the R1 gene using allele specific primers 76-2sf2 and 76-2SR and template DNA of (A) Desirée; (B) resistant parent P41; (C) susceptible parent P40; (D) transgenic Desirée plant 10-2__5; (E) BAC clone BA87d17 carrying the R1 allele; (F), (G), (H), (I), (J) BAC clones BA122p13, BA12101, BA76011, BA47F2 and BA27c1, respectively, (K) negative control.

PCR primers specific for cDNA c76-2 were designed based on sequence alignment with the other seven candidate cDNAs. Primers 76-2sf2 and 76-2SR (see Material and Methods) generated a 1.4 kb PCR product only in parent P41 (R1r1) but not in parent P40 (r1r1) (FIG. 2). This polymorphism suggested the possibility that BAC BA87d17 (derived from the R1 hosting chromosome) contained the R1 gene, even if the mapping data still indicated absence of recombination between the distal end of this BAC clone and R1.

Example 4

Complementation of the R1 Phenotype

A genomic sub-library in the pCLD04541 binary vector (see Material and Methods) with, on average, 10 kb insertions was constructed from BA87d17 (76 kb). The library was screened by colony hybridisation with the RGL probe of BA121o1. Positive clones were evaluated for the presence of the complete copy of the candidate RGL gene by the size of amplification products obtained by PCR with forward primers from the vector borders (T3 and T7) and reverse primers from the RGL. Clones were also tested by using the c76-2 cDNA specific primers 76-2sf2 and. 76-2SR. Subclone g10-2 was selected and transformed into *A. tumefaciens*. Three different, bacterial colonies were used to transform the susceptible cultivar Desirée. From three transformation experiments, fifteen independent transgenic lines were regenerated and tested in four independent experiments for expression of resistance to *P. infestans* race 4 (Table 2).

Table 2. Test for resistance to *P. infestans* race 4 of transgenic potato lines transformed with clone g10. Transgenic lines were tested in four independent experiments with three leaflets from each line for expression of hypersensitive resistance to *P. infestans* race 4.

TABLE 2

Test for resistance to *P. infestans* race 4 of transgenic potato lines transformed with clone g10. Transgenic lines were tested in four independent experiments with three leaflets from each line for expression of hypersensitive resistance to *P. infestans* race 4.

| Transgenic line | no | Resistance[c] |
|---|---|---|
| 10-2[a] | 1[b] | S |
| 10-2 | 2 | R |

TABLE 2-continued

Test for resistance to *P. infestans* race 4 of transgenic potato lines transformed with clone g10. Transgenic lines were tested in four independent experiments with three leaflets from each line for expression of hypersensitive resistance to *P. infestans* race 4.

| Transgenic line | no | Resistance[c] |
|---|---|---|
| 10-2 | 3 | R |
| 10-2 | 4 | R |
| 10-5 | 1 | R |
| 10-5 | 2 | S |
| 10-5 | 3 | n.d. |
| 10-5 | 4 | n.d. |
| 10-5 | 5 | R |
| 10-23 | 1 | n.d. |
| 10-23 | 2 | R |
| 10-23 | 3 | R |
| 10-23 | 4 | R |
| 10-23 | 5 | R |
| 10-23 | 6 | S |

Figure 3:
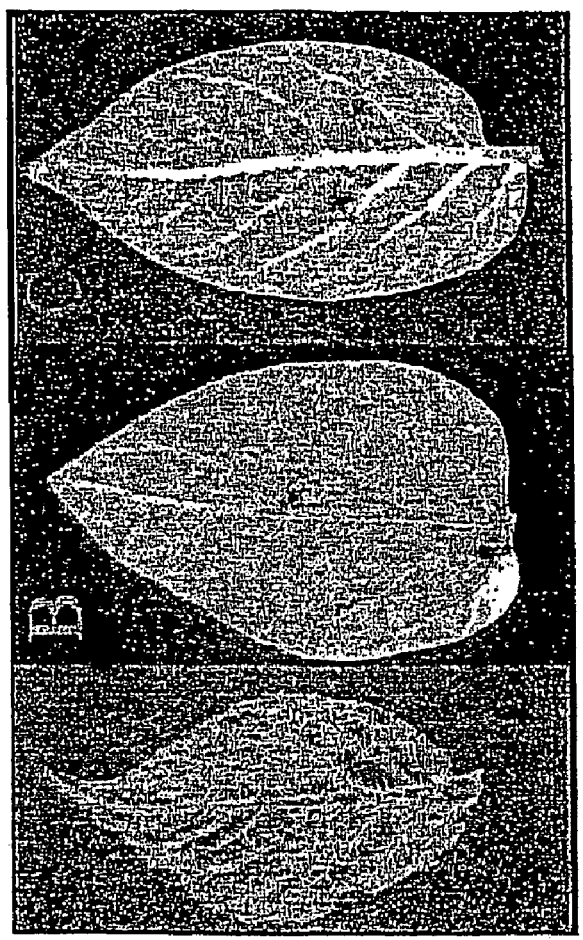
FIG. 3. R1 complementation test. Disease symptoms are shown 9 days post-inoculation on leaflets from (A) susceptible Desirée; (B) transgenic Desirée line no 10-2__5 transformed with clone g10-2 and (C) the resistant parent P41 (R1r1).

Nine transgenic lines showed consistently a typical HR response, similar to the resistant line P41 hosting R1 (FIG. 3); three gave inconsistent results and the remaining three were susceptible, like the untransformed Desirée control. Based on these results, it was concluded that the subclone g10 contained a functional R1 gene.

All transgenic lines with the R1 phenotype contained the gene corresponding to cDNA 76-2, as demonstrated by presence of the, 1.4 kb PCR product amplified by primers 76-2sf2 and 76-2SR. This product was absent in untransformed Desirée (control) and in all BAC clones reported in FIG. 1 as members of the contig around R1, except for BA87d17 (FIG. 2).

Example 5

Structure of the R1 Gene

Subclone g10 containing the R1 gene was sequenced; see SEQ ID NO: 1. The sequence was 10,388 nucleotides long and contained one gene with sequence similarity to other plant resistance genes. No other open reading frame or sequence homology was identified in the GenEMBL database. Sequence alignment with the cDNA c76-2 and the 5' RACE product revealed the presence of three exons and three introns. Two introns of 92 bp (position 4878 to 4970) and 126 bp (position 6103 to 6229) interrupt the coding region. The third intron of 81 bp (position 6323 to 6404) is located in the 3'untranslated region immediately downstream of the stop codon (FIG. 4A). The deduced amino acid sequence predicts a polypeptide of 1293 amino acids with a molecular mass of 149.4 kDa (FIG. 4B). The deduced amino acid sequence of the R1 gene is most similar (40% identity) to the Prf gene for resistance to *P. syringae* of tomato (Salmeron et al. 1996). The predicted R1 protein has a putative nucleotide binding site (NBS) domain consisting of P-loop (amino acids 572-578), kinase 2 (amino acids 649-65.3) and kinase 3a (amino acids 677-682) motifs (FIG. 4B). Downstream of the kinase motifs were other sequences with similarity to domains of unknown function conserved among resistance genes: GLPL (QLPL (SEQ ID NO: 10) in R1), CR1) and MHD (LHD in R1). Searching for conserved motifs by using the ExPASY algorithm, 4 myristylation, 9 glycosylation, 43 phosphorylation and 1 amidation putative sites were found in the deduced R1 amino acid sequence. The putative leucine rich repeat (LRR) domain of R1 has 15-16 imperfect repeats located in the carboxy-terminal part of the gene. Like some plant R-proteins with cytoplasmic LRRs, the R1 protein contains a leucine zipper from amino acid position 308 to 329 (Hammond-Kosack and Jones, 1997). KLY (CFLY (SEQ ID NO: 12) in

Example 6

Genomic Organization of the R1 Focus

Southern gel blot analysis showed that R1 is a member of a gene family.

Figure 5:
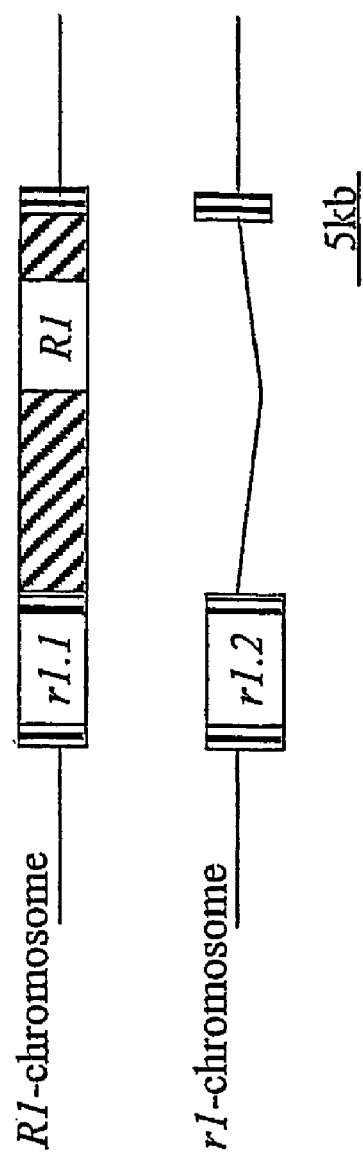
FIG. 5. Schematic representation of the chromosome 5 region around the R1 locus. Boxes filled with vertical lines represent homologous regions between the chromosomes bearing the R1 and r1 alleles. The functional allele R1.1 and the R1.2/r1.2 locus are marked with opened boxes. The angled line indicates the deletion present on the r1-chromosome when compared to the R1-chromosome.

The R1 specific primers 76-2sf2 and 76-2SR amplified the 1.4 kb fragment in BA87d17 (R1) but not in the overlapping clones BA121o1, BA122p13 and BA76o11 (r1) (FIG. 2). DNA sequence analysis of BACs BA87d17 (R1) and BA122p13 (r1) revealed that BA87d17 contained two highly homologous members of the R1 gene family, R1 corresponding to the functional R1 gene and r1.1 being orthologous with the r1.2 allele in BA122p13. The functional R1 gene was part of a 15 kb insertion present in the R1 bearing chromosome in the region represented by BA87d17, but absent in the chromosome hosting r1 (FIG. 5).

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, sequences or other disclosures) in the Background of the Invention, Description, Examples, and Sequence Listing is hereby incorporated herein by reference.

REFERENCES

Appel, R-D., Bairoch, A. and Hochstrasser, D. F. (1994). A new generation of information retrieval tools for biologists: the example of the ExPASY www server. Trends Biochem. Sci. 19:258-260

Balivora, A., Schornack, S., Baker, B. J., Ganal, M., Bonas, U. and Lahaye, T. (2001) Chromosome landing at the tomato Bs4 locus. Mol Gen Genet, in press.

Bendahmane, A., Kanyuka, K. and Baulcombe, D. C. (1999) The Rx gene from potato controls separate virus resistance and cell death responses. The Plant Cell 11: 781-791

Bendahmane, A., Querci, M., Kanyuka, K. and Baulcombe, D. C. (2000) Agrobacterium transient expression system as a tool for the isolation of disease resistance genes: application to the Rx2 locus in potato. The Plant Journal 21: 73

Dangl, J. L. and Jones, J. D. G. (2001). Plant pathogens and integrated defence responses to infection. Nature 411:826-833

De Jong, W., Forsyth, A., Leister, D, Gebhardt, C. and Baulcombe, D. C. (1997). A potato hypersensitive resistance gene against potato virus X maps to a resistance gene cluster on chromosome V. Theor Appl Genet 95:153-62.

Dong F, Song J, Naess S K, Helgeson J P, Gebhardt C, Jiang J (2000) Development and applications of a set of chromosome-specific cytogenetic DNA markers in potato. Theor Appl Genet 101: 1001-07.

El-Kharbotly, A., Leonards-Schippers, C., Huigen, D. J., Jacobsen, E., Pereira, A., Stiekema, W. J., Salamini, F. and Gebhardt, C. (1994). Segregation analysis and RFLP mapping of the R1 and R3 alleles conferring race specific resistance to *Phytophthora infestans* in progenies of dihaploid potato parents. Mol. Gen. Genet. 242: 749-754.

El-Kharbotly, A., Palomino-Sanchez, C., Salamini, F., Jacobsen, E. and Gebhardt, C. (1996). R6 and R7 alleles of potato conferring race-specific resistance to *Phytophthora infestans* (Mont.) de Bary identified genetic loci clustering with the R3 locus on chromosome XI. Theor Appl Genet 92: 880-884.

Ellis, J. G., Lawrence, G. J., Luck, J. E. and Dodds, P. N. (1999). Identification of regions in alleles of the flax rust resistance gene L that determine differences in gene-for-gene specificity. Plant Cell 11:495-506

Ellis, J. G., Dodds, P. N. and Pryor, T. (2000). Structure, function and evolution of plant disease resistance genes. Curr Opin Plant Biol 3:278-284

Ewing, E. E., Simko, I., Smart, C. D., Bonierbale, M. W., Mizubuti, E. S. G., May, G. D., and Fry, W. E. (2000). Genetic mapping from field tests of quantitative and qualitative resistance to *Phytophthora infestans* in a population derived from *Solanum tuberosum* and *Solanum berthaultii*. Mol Breeding 6: 25-36.

Feinberg, A. P. and Vogelstein, B. (1984). A technique for radiolabeling DNA restriction endonuclease fragments to high specific activity (addendum). Anal Biochem 137: 266-267.

Flor, H. H (1971) Current status of the gene-for-gene concept. Annu Rev Phytopathol 9: 275-296

Folkertsma, R. T., Spassova, M. I., Prins, M., Stevens, M. R., Hille, J. and Goldbach R. W. (1999). Construction of a bacterial artificial chromosome (BAC) library of *Lycopersicon esculentum* cv. Stevens and its application to physically map the Sw-5 locus. Molecular Breeding 5:197-207

Fry, W. E. and Goodwin, S. B. (1997). Resurgence of the Irish potato famine fungus. Bioscience 47: 363-371.

Gebhardt, C., Ritter, E., Debener, T., Schachtschabel, U., Walkemeier, B., Uhrig, U. and Salamini, F. (1989). RFLP analysis and linkage mapping in *Solanum tuberosum*. Theor Appl Genet 78:65-75

Gebhardt, C. and Valkonen, J. P. T. (2001). Organization of genes controlling disease resistance in the potato genome. Annu Rev. Phytopathol. 39: 79-102.

Hammond_Kosack, K. and Jones, J. D. (1997). Plant disease resistance genes Annu Rev Plant Physiol Plant Mol Biol 48: 575-607

Jones, D. A., Thomas, C. M., Hammond-Kosack. K. E., Balint-Kurti, P. J. and Jones, D. J. G. (1992). Effective vectors for transformation, expression of heterologous genes, and assaying transposon excision in transgenic plants. Transgenic Res. 1:285-297

Jones, D. A. and Jones, D. J. G. (1997). The roles of leucine rich repeats in plant defences. Adv Bot Res Adv Plant Pathol 24:90-167

Judelson, H. S. (1997). The genetics and biology of *Phytophthora infestans*: Modern approaches to a historical challenge. Fungal Genet and Biol 22: 65-76.

Kamoun, S. (2001). Nonhost resistance to *Phytophthora*: Novel prospects for a classical problem. Curr Opin Plant Biol 4:295-300

Kreike, C. M., De Koning, J. R. A., Vinke, J. H., Van Ooijen, J. W., and Stiekema, W. J. (1994). Quantitatively-inherited resistance to *Globodera pallida* is dominated by one major locus in *Solanum spegazzinii*. Theor Appl Genet 88: 764-69.

Kozak, M. (1991) Structural features in eukaryotic mRNAs that modulate the initiation of translation. J Biol Chem 266:19867-19870

Leister, D., Ballvora, A., Salamini., F, and Gebhardt, C. (1996). A PCR based approach for isolating pathogen resistance genes from potato with potential for wide application in plants. Nature Genetics 14: 421-429.

Leister, D., Berger, A., Thelen, H., Lehmann, W., Salamini, F. and Gebhardt, C. (1997). construction of a potato YAC library and identification of clones linked to the disease resistance loci R1 and Gro1. Theor Appl Genet 95; 954-960.

Leonards-Schippers, C., Gieffers, W., Gebhardt, C. and Salamini, F. (1992). The R1 gene conferring race-specific resistance to *Phytophtora infestans* in potato is located on potato chromosome V. Mol Gen Genet 233:278-283

Leonards-Schippers, C., Gieffers, W., Schäfer-Pregl, R., Ritter, E., Knapp, S. J., Salamini, F. and Gebhardt, C. (1994). Quantitative resistance to *Phytophthora infestans* in potato: a case study for QTL mapping in an allogamous plant species. Genetics 137: 67-77.

Li, X., van Eck, H. J., Rouppe van der Voort, J., Huigem, D-J., Stam, P., and Jacobsen, E. (1998). Autotetraploids and genetic mapping using common AFLP markers: The R2 allele conferring resistance to *Phytophthora infestans* mapped on potato chromosome 4. Theor App Genet 96: 1121-28.

Meksem, K. Leister, D. Peleman, J., Zabeau, M., Salamini, F. and Gebhardt, C. (1995). A high-resolution map of the vicinity of the R1 locus on chromosome V of potato based on RFLP and AFLP markers Mol Gen Genet 249:74-81

Meksem, K., Zobrist, K., Ruben, E. Hyten, D., Quanzhou, T., Zhang, H-B. and Lightfoot, D. A. (2000). Two large-insert soybean genomic libraries constructed in a binary vector: applications in chromosome walking and genome wide physical mapping. Theor Appl Genet 101:747-755

Naess, S. K., Bradeen, J. M., Wielgus, S. M., Haberlach, G. T., McGrath, J. M., and Helgeson, J. P. (2000). Resistance to late blight in *Solanum bulbocastanum* is mapped to chromosome 8. Theor Appl Genet 101: 697-704.

Nakamura, S., Asakawa, S., Ohmido, N., Fukui, K., Shimizu, N. and Kawasaki, S. (1997). Construction of an 800-kb contig near-centromeric region of the rice blast resistance gene Pi-ta$^2$ using a highly representative rice BAC library. Mol Gen Genet 254:611-620

Oberhagemann, P., Chatot-Balandras, C., Bonnel, E., Schäfer-Pregl, R., Wegener, D., Palomino, C., Salamini, F. and Gebhardt, C. (1999). A genetic analysis of quantitative resistance to late blight in potato: Towards marker assisted selection. Mol Breed 5: 399-415.

Person, C., Samborski, D. J. and Rohringer, R. (1962) The gene-for-gene concept. Nature 194: 561-562

Rocha-Sosa, M., Sonnewald, U., Frommer, W., Stratmann, M., Schell, J. and Willmitzer, L. (1989). Both developmental and metabolic signals activate the promoter of a class I patatin gene. The EMBO Journal 8 (1):23-29.

Ross, H. (1986). Potato breeding. Problems and perspectives. *Adv Plant Breed*, Supplement 13.

Reiser, L., Modrusan, Z., Margossian, L., Samach, A., Ohad, N., Haughn, G. W. and Fischer, R. (1995). The BELL1 Gene Encodes a Homeodomain Protein involved in Pattern Formation in the *Arabidopsis* Ovule Primordium. Cell 83:735-742

Ritter, E., Debener, T., Barone, A., Salamini, F. and Gebhardt, C. (1991). RFLP mapping on potato chromosomes of two genes controlling extreme resistance to potato virus X (PVX). Mol Gen Genet 227: 81-85.

Rouppe van der Voort, J., Wolters, P., Folkertsma, R., Hutten, R., van Zandvoort, P., Vinke, H., Kanyuka, K., Bendahmane, A., Jacobsen, E., Janssen, R. and Bakker, J. (1997). Mapping of the cyst nematode resistance locus Gpa2 in potato using a strategy based on comigrating AFLP markers. Theor Appl Genet 95: 874-80.

Rouppe van der Voort, J., van der Vossen, E. Bakker, E., Overmars, H., van Zandvoort, P., Hutten, R., Klein-Lankhorst, R. and Bakker, J. (2000). Two additive. QTLs conferring broad-spectrum resistance in potato to *Globodera pallida* are localized on resistance gene clusters. Theor Appl Genet 101: 1122-30.

Salaman, R. N. (1985). The potato famine: its causes and consequences. In The History and Social Influence of the Potato, revised impression, ed. J G Hawkes, pp 289-316. Cambridge/New York/New Rochelle/Melbourne/Sydney: Cambridge University Press.

Salmeron, J. M., Oldroyd, O. E., Rommens C. M., Scofield, S. R., Kim, H-S., Lavelle, D. T., Dahlbeck, D. and Staskawicz, B. J. (1996). Tomato Prf is a member of the leucine-rich repeat class of plant disease resistance genes and lies embedded within the Pto kinase gene cluster. Cell, Vol. 86:123-133

Sambrook, J., Fritsch, E. F. and Maniatis, T. (1989). Molecular Cloning: A laboratory Manual. (Cold Spring Harbor, N.Y.: Cold Spring Harbor Laboratory Press).

Singh, A. K., Salamini, F. and Uhrig, H. (1989). Chromosome pairing in 14 F1 hybrids among 11 diploid potato species. J Genet Breed 43:1-5

Stahl, E. A., Dwyer, G., Mauricio, R., Kreitman, M. and Bergelson, J. (1999) Dynamics of disease resistance polymorphism at the Rpm1 locus in *Arabidopsis*. Nature 400:667-671

Tanksley S D, Ganal M W, Prince J P, de Vicente M C, Bonierbale M W, Broun P, Fulton T M, Giovannoni J J, Grandillo S, Martin G B, Messeguer R, Miller J C, Miller L, Paterson A H, Pineda O, Röder M S, Wing R A, Wu W, Young N D. 1992. High density molecular linkage maps of the tomato and potato genomes. Genetics 132: 1141-60.

Van der Lee, T., Robold, A., Testa, A., van't Klooster, J. W. and Govers, F. (2001). Mapping of Avirulece Genes in *Phytophthora infestans* With Amplified Fragment Length Polymorphism Markers Selected by Bulked. Segregant Analysis. Genetics 157: 949-956

Van der Vossen, E. A. G., Rouppe van der Voort, J. N. A. M., Kanyuka, K., Bendahmane, A., Sandbrink, H., Baulcombe, D. C., Bakker, J., Stiekema, W. J. and Klein-Lankhorst, R. M. (2000) Homologues of a single resistance-gene cluster in potato confer resistance to distinct pathogens: a virus and a nematode. The Plant Journal 23: 567-576

Wastie, R. L. (1991). Breeding for resistance. Adv Plant Pathol 7: 193-223.

Wen-jun, S. and Forde, B. G. (1989). Efficient transformation of *Agrobacterium* spp. By high voltage electroporation. Nuc Acids Res 17:8385

Yang, D., Parco, A., Nandi, S., Subudhi, P., Zhu, Y., Wang, G. and Huang, N. (1997). Construction of a bacterial artificial chromosome (BAC) library and identification of overlapping BAC clones With chromosome 4-specific RFLP markers Yang, D., Sanzhes, A., Khush, G. S., Zhu, Y., and Huang, N. (1998). Construction of a BAC contig containing the xa5 locus in rice. Theor Appl Genet 97:1120-1124.

The invention claimed is:

1. An isolated nucleic acid molecule encoding a polypeptide which confers resistance against a pathogen in a plant in which said polypeptide is expressed, said nucleic acid molecule comprising a nucleotide sequence selected from the group consisting of:
   - (a) a nucleotide sequence encoding the amino acid sequence of SEQ ID NO: 2;
   - (b) the nucleotide sequence of SEQ ID NO: 1; and
   - (c) a nucleotide sequence encoding a polypeptide having an amino acid sequence at least 95% identical to the amino acid sequence of SEQ ID NO: 2, wherein the polypeptide has pathogen resistance activity.

2. The isolated nucleic acid molecule of claim 1 wherein said pathogen is *Phytophthora infestans*.

3. A vector comprising the isolated nucleic acid molecule of any one of claim 1 or 2.

4. The vector of claim 3 which is an expression vector wherein the nucleic acid molecule is operatively linked to one or more control sequences.

5. The host cell comprising the vector of claim 3.

6. A transgenic plant cell comprising the isolated nucleic acid molecule of any one of claims 1 or 2 which is operably linked to regulatory elements.

7. A transgenic plant or a plant tissue comprising the plant cell of claim 6.

* * * * *